United States Patent
Ma et al.

(10) Patent No.: US 11,869,191 B2
(45) Date of Patent: *Jan. 9, 2024

(54) SYSTEM AND METHOD FOR TISSUE VIABILITY SCREENING

(71) Applicant: THE REGENTS OF THE UNIVERSITY OF CALIFORNIA, Oakland, CA (US)

(72) Inventors: Ning Ma, Oakland, CA (US); Michelle Digman, Oakland, CA (US); Hongtao Chen, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,743

(22) Filed: Jul. 11, 2022

(65) Prior Publication Data

US 2023/0129517 A1    Apr. 27, 2023

Related U.S. Application Data

(63) Continuation of application No. 16/839,463, filed on Apr. 3, 2020, now Pat. No. 11,386,559.
(Continued)

(51) Int. Cl.
*G06K 9/00* (2022.01)
*G06T 7/00* (2017.01)
(Continued)

(52) U.S. Cl.
CPC ....... *G06T 7/0014* (2013.01); *G01N 21/6486* (2013.01); *G01N 33/5005* (2013.01);
(Continued)

(58) Field of Classification Search
CPC . G06T 2207/10064; G06T 2207/20048; G06T 2207/20052; G06T 2207/20056;
(Continued)

(56) References Cited

U.S. PATENT DOCUMENTS

2012/0276578 A1    11/2012  Stringari
2014/0206931 A1*    7/2014  Zernicka-Goetz ..... C12M 41/14
                                                              506/10
(Continued)

OTHER PUBLICATIONS

C. G. Vergouw et al., Metabolomic profiling by near-infrared spectroscopy as a tool to assess embryo viability: a novel, non-invasive method for embryo selection. Hum Reprod 23, 1499-1504 (2008).
(Continued)

*Primary Examiner* — Atiba O Fitzpatrick
(74) *Attorney, Agent, or Firm* — Riverside Law, LLP

(57) ABSTRACT

A system for determining the viability of an embryo comprises an imaging device, an excitation device configured to direct an excitation energy at an embryo, a controller communicatively connected to the imaging device and the excitation device, configured to drive the excitation device and collect images from the imaging device at an imaging frequency, a processor performing steps comprising acquiring a set of images from the imaging device, performing a Fourier Transformation to generate a set of phasor coordinates, computing a D-trajectory, computing a set of values of additional parameters, comparing the set of values to a set of stored values related to embryos of known viability, and calculating a viability index factor of the embryo from the set of values and the set of stored values. Methods of calculating embryo viability and determining one or more properties of a tissue are also described.

14 Claims, 22 Drawing Sheets

Specification includes a Sequence Listing.

Related U.S. Application Data

(60) Provisional application No. 62/828,848, filed on Apr. 3, 2019.

(51) Int. Cl.

| | | |
|---|---|---|
| *G01N 33/50* | (2006.01) | |
| *G01N 21/64* | (2006.01) | |
| *G06T 7/66* | (2017.01) | |
| *H04N 23/56* | (2023.01) | |

(52) U.S. Cl.
CPC ............... *G06T 7/66* (2017.01); *H04N 23/56* (2023.01); *G06T 2207/10056* (2013.01); *G06T 2207/10064* (2013.01); *G06T 2207/20056* (2013.01); *G06T 2207/30024* (2013.01); *G06T 2207/30044* (2013.01)

(58) Field of Classification Search
CPC ................. G06T 7/0014; G06T 7/0016; G06T 2207/30024; G06T 2207/10056; G01N 21/64; G01N 21/6402; G01N 21/6404; G01N 2021/6406; G01N 21/6408; G01N 2021/6413; G01N 2021/6439; G01N 21/6445; G01N 21/6486; G01N 21/6428; G01N 21/6458; G01N 21/6456; G01N 33/582; G01N 2201/06193; G01N 33/5005; G01N 33/5008; G01N 33/5038; G01N 33/5073; G01N 33/5044; G01N 33/502; G01N 33/5735; G01N 33/573; G01N 33/53; G01N 33/50; G01N 33/483; G01N 33/4833; G01N 33/4836; G01N 15/10; G01N 2015/1006; G01J 3/4406; G01J 3/44; A61B 5/0071; A61B 5/0059; C12M 1/3476; G06V 20/698; G06V 20/69; G16H 50/70; G16H 50/30; G16H 50/20; G16H 50/00; G16H 10/40; G16H 10/00
See application file for complete search history.

(56) References Cited

U.S. PATENT DOCUMENTS

| | | | |
|---|---|---|---|
| 2014/0363840 A1 | 12/2014 | Mycek | |
| 2015/0160117 A1* | 6/2015 | Wong ................... | C12Q 1/6881 435/29 |
| 2015/0346100 A1* | 12/2015 | Racowsky ......... | G01N 21/6486 435/34 |
| 2018/0120228 A1 | 5/2018 | Racowsky | |
| 2019/0287222 A1 | 9/2019 | Cutrale | |
| 2021/0249135 A1* | 8/2021 | Rimestad ................ | G16H 50/20 |

OTHER PUBLICATIONS

C. Stringari et al., Metabolic trajectory of cellular differentiation in small intestine by Phasor Fluorescence Lifetime Microscopy of NADH. Sci Rep 2, 568 (2012).
C. Stringari et al., Phasor approach to fluorescence lifetime microscopy distinguishes different metabolic states of germ cells in a live tissue. Proc Natl Acad Sci U S A 108, 13582-13587 (2011).
C. Stringari, J. L. Nourse, L. A. Flanagan, E. Gratton, Phasor fluorescence lifetime microscopy of free and protein-bound NADH reveals neural stem cell differentiation potential. PLoS One 7, e48014 (2012).
C. Stringari, R. Sierra, P. J. Donovan, E. Gratton, Label-free separation of human embryonic stem cells and their differentiating progenies by phasor fluorescence lifetime microscopy. J Biomed Opt 17, 046012 (2012).
D. K. Gardner, M. Lane, I. Calderon, J. Leeton, Environment of the preimplantation human embryo in vivo: metabolite analysis of oviduct and uterine fluids and metabolism of cumulus cells. Fertil Steril 65, 349-353 (1996).
D. K. Gardner, M. Lane, J. Stevens, T. Schlenker, W. B. Schoolcraft, Blastocyst score affects implantation and pregnancy outcome: towards a single blastocyst transfer. Fertility and sterility 73, 1155-1158 (2000).
D. K. Gardner, P. L. Wale, Analysis of metabolism to select viable human embryos for transfer. Fertil Steril 99, 1062-1072 (2013).
E. Seli et al., Noninvasive metabolomic profiling as an adjunct to morphology for noninvasive embryo assessment in women undergoing single embryo transfer. Fertil Steril 94, 535-542 (2010).
E. Seli et al., Noninvasive metabolomic profiling of embryo culture media using Raman and near-infrared spectroscopy correlates with reproductive potential of embryos in women undergoing in vitro fertilization. Fertil Steril 88, 1350-1357 (2007).
E. Sonoda et al., Collaborative roles of gammaH2AX and the Rad51 paralog Xrcc3 in homologous recombinational repair. DNA Repair (Amst) 6, 280-292 (2007).
G. Sher, L. Keskintepe, M. Nouriani, R. Roussev, J. Batzofin, Expression of sHLA-G in supernatants of individually cultured 46-h embryos: a potentially valuable indicator of 'embryo competency' and IVF outcome. Reproductive biomedicine online 9, 74-78 (2004).
H. Esterbauer, Cytotoxicity and genotoxicity of lipid-oxidation products. Am J Clin Nutr 57, 779S-785S; discussion 785S-786S (1993).
H. J. Leese, A. M. Barton, Pyruvate and glucose uptake by mouse ova and preimplantation embryos. J Reprod Fertil 72, 9-13 (1984).
I. Revet et al., Functional relevance of the histone gammaH2Ax in the response to DNA damaging agents. Proc Natl Acad Sci U S A 108, 8663-8667 (2011).
J. M. Squirrell, D. L. Wokosin, J. G. White, B. D. Bavister, Long-term two-photon fluorescence imaging of mammalian embryos without compromising viability. Nat Biotechnol 17, 763-767 (1999).
K. Ko nig, P. C. So, W. Mantulin, B. Tromberg, E. Gratton, Two-photon excited lifetime imaging of autofluorescence in cells during UV A and NIR photostress. Journal of microscopy 183, 197-204 (1996).
L. A. Scott, S. Smith, The successful use of pronuclear embryo transfers the day following oocyte retrieval. Human Reproduction 13, 1003-1013 (1998).
L. Botros, D. Sakkas, E. Seli, Metabolomics and its application for non-invasive embryo assessment in IVF. Molecular human reproduction 14, 679-690 (2008).
L. Covarrubias, D. Herna ndez-Garcí a, D. Schnabel, E. Salas-Vidal, S. Castro-Obrego n, Function of reactive oxygen species during animal development: passive or active? Developmental biology 320, 1-11 (2008).
M. A. Digman, V. R. Caiolfa, M. Zamai, E. Gratton, The phasor approach to fluorescence lifetime imaging analysis. Biophysical journal 94, L14-L16 (2008).
M. Chiang et al., Analysis of in vivo single cell behavior by high throughput, human-in-the-loop segmentation of three-dimensional images. BMC Bioinformatics 16, 397 (2015).
M. Lane, D. K. Gardner, Lactate Regulates Pyruvate Uptake and Metabolism in the PreimplantationMouse Embryo. Biology of reproduction 62, 16-22 (2000).
M. Lane, D. K. Gardner, Mitochondrial malate-aspartate shuttle regulates mouse embryo nutrient consumption. Journal of Biological Chemistry 280, 18361-18367 (2005).
M. Y. Berezin, S. Achilefu, Fluorescence lifetime measurements and biological imaging. Chem Rev 110, 2641-2684 (2010).
N. Shyh-Chang, G. Q. Daley, L. C. Cantley, Stem cell metabolism in tissue development and aging. Development 140, 2535-2547 (2013).
Office Action (Notice of Allowance and Fees Due (PTOL-85)) dated Mar. 1, 2022 for U.S. Appl. No. 16/839,463 (pp. 1-7).
Office Action dated Nov. 12, 2021 for U.S. Appl. No. 16/839,463 (pp. 1-8).
P. D. Ray, B.-W. Huang, Y. Tsuji, Reactive oxygen species (ROS) homeostasis and redox regulation in cellular signaling. Cellular signalling 24, 981-990 (2012).

(56) References Cited

OTHER PUBLICATIONS

P. De Sutter, D. Dozortsev, C. Qian, M. Dhont, Oocyte morphology does not correlate with fertilization rate and embryo quality after intracytoplasmic sperm injection. Human Reproduction 11, 595-597 (1996).

P. L. Wale, D. K. Gardner, The effects of chemical and physical factors on mammalian embryo culture and their importance for the practice of assisted human reproduction. Hum Reprod Update 22, 2-22 (2016).

R. Datta, A. Alfonso-Garcia, R. Cinco, E. Gratton, Fluorescence lifetime imaging of endogenous biomarker of oxidative stress. Sci Rep 5, 9848 (2015).

R. Dumollard, J. Carroll, M. Duchen, K. Campbell, K. Swann, in Seminars in cell & developmental biology. (Elsevier, 2009), vol. 20, pp. 346-353.

R. R. Gonzalez et al., Leptin and leptin receptor are expressed in the human endometrium and endometrial leptin secretion is regulated by the human blastocyst 1. The Journal of Clinical Endocrinology & Metabolism 85, 4883-4888 (2000).

R. Scott et al., Noninvasive metabolomic profiling of human embryo culture media using Raman spectroscopy predicts embryonic reproductive potential: a prospective blinded pilot study. Fertil Steril 90, 77-83 (2008).

S. Ranjit, A. Dvornikov, M. Levi, S. Furgeson, E. Gratton, Characterizing fibrosis in UUO mice model using multiparametric analysis of phasor distribution from FLIM images. Biomedical Optics Express 7, 3519-3530 (2016).

T. Baczkowski, R. Kurzawa, W. Głabowski, Methods of embryo scoring in in vitro fertilization. Reprod Biol 4, 5-22 (2004).

T. Hamaoka, K. K. McCully, V. Quaresima, K. Yamamoto, B. Chance, Near-infrared spectroscopy/imaging for monitoring muscle oxygenation and oxidative metabolism in healthy and diseased humans. J Biomed Opt 12, 062105 (2007).

T. Watanabe et al., Characterisation of the dynamic behaviour of lipid droplets in the early mouse embryo using adaptive harmonic generation microscopy. BMC Cell Biol 11, 38 (2010).

Z. W. Wang et al., Laser microbeam-induced DNA damage inhibits cell division in fertilized eggs and early embryos. Cell Cycle 12, 3336-3344 (2013).

\* cited by examiner

703

704

SEQUENCE LISTING

```
Sequence total quantity: 4
SEQ ID NO: 1            moltype = DNA   length = 19
FEATURE                 Location/Qualifiers
source                  1..19
                        mol_type = other DNA
                        organism = synthetic construct
SEQUENCE: 1
atgagcgtgg tggttatgc                                                   19

SEQ ID NO: 2            moltype = DNA   length = 18
FEATURE                 Location/Qualifiers
source                  1..18
                        mol_type = other DNA
                        organism = synthetic construct
SEQUENCE: 2
gatggttcgg ataatgcg                                                    18

SEQ ID NO: 3            moltype = DNA   length = 20
FEATURE                 Location/Qualifiers
source                  1..20
                        mol_type = other DNA
                        organism = synthetic construct
SEQUENCE: 3
aagcctaaga tgagcgcaag                                                  20

SEQ ID NO: 4            moltype = DNA   length = 20
FEATURE                 Location/Qualifiers
source                  1..20
                        mol_type = other DNA
                        organism = synthetic construct
SEQUENCE: 4
aagcgacaat ctaccagagg                                                  20
```

SYSTEM AND METHOD FOR TISSUE VIABILITY SCREENING

CROSS-REFERENCE TO RELATED APPLICATIONS

This application is a divisional of U.S. patent application Ser. No. 16/839,463, filed on Apr. 3, 2020, which claims priority to U.S. Provisional Patent Application No. 62/828,848, filed on Apr. 3, 2019, each of which are incorporated herein by reference in their entirety.

STATEMENT REGARDING FEDERALLY SPONSORED RESEARCH OR DEVELOPMENT

This invention was made with government support under grant nos. R21HD090629 and 2P41GM103540 from the National Institutes of Health. The government has certain rights in the invention.

REFERENCE TO A "SEQUENCE LISTING", A TABLE, OR A COMPUTER PROGRAM LISTING APPENDIX SUBMITTED AS AN XML FILE

The present application hereby incorporates by reference the entire contents of the XML file named "206101-0026-01US_SequenceListing.xml" in XML format, which was created on Nov. 10, 2022, and is 4,648 bytes in size.

BACKGROUND OF THE INVENTION

It is estimated that more than 8 million babies have been born worldwide since the first in-vitro fertilization (IVF) baby was born in 1978. The latest figure is that around 1.5 million Assisted Reproductive Technology (ART) cycles are performed each year worldwide, with an estimated 350,000 babies born.

Determining embryo quality during in vitro fertilization (IVF) is one of the most important steps toward successful pregnancy. The standard non-invasive method to assess embryo quality and viability relies on the visual inspection of embryo morphology according to predefined criteria such as cell division patterns, the number of pronucleoli in cleavage stages, and the physical characteristics of the blastocyst. Assisted reproduction through morphological evaluation is labor-intensive and highly dependent on the performance of individual physicians trained in these techniques. Development of more quantitative and objective means for assessing embryo quality that are simpler, safer, and faster could provide significant advantages in assisted reproduction by enabling single embryo transfers rather than the implantation of multiple embryos in order to increase the likelihood of a successful pregnancy.

Given the limitations of morphological evaluation, several technologies have been explored for the assessment of embryo viability. These include the measurement of metabolites in embryonic culture media, as well as genomic and proteomic profiling of the embryos themselves. Other spectroscopic technologies have emerged as a non-invasive means of revealing embryo viability via the detection of various metabolic states of common molecules associated with embryo development. Raman, near-infrared, Nuclear Magnetic Resonance (NMR), and Fourier-transform infrared spectroscopy can also detect the metabolic states of pyruvate, lactate, glucose, and oxygen during pre-implantation mammalian development (see e.g. E. Seli et al., Noninvasive metabolomic profiling of embryo culture media using Raman and near-infrared spectroscopy correlates with reproductive potential of embryos in women undergoing in vitro fertilization. Fertil Steril 88, 1350-1357 (2007); C. G. Vergouw et al., Metabolomic profiling by near-infrared spectroscopy as a tool to assess embryo viability: a novel, non-invasive method for embryo selection. Hum Reprod 23, 1499-1504 (2008); and E. Seli et al., Noninvasive metabolomic profiling as an adjunct to morphology for noninvasive embryo assessment in women undergoing single embryo transfer. Fertil Steril 94, 535-542 (2010), all incorporated herein by reference). However, at the present time these technologies suffer from a number of shortcomings. It is challenging for these approaches to analyze the data in the short time window needed for the host transfer of embryos. The data analyses are technically demanding and may not be intuitively obvious for the general clinical use. The technologies require fluid samples collected from the embryo culture media and the data are inherently noisier.

Fluorescence Lifetime Imaging Microscopy (FLIM) produces an image, based on the exponential decay rates at each pixel from a fluorescent sample. The fluorescence lifetime of the fluorophore signal is measured to create the image via FLIM. An exemplary illustration of phasor FLIM analysis is shown in FIG. 2. During FLIM collection, a pulsed 2-photon laser is used to measure the intensity at short time windows (time arrival of the photons) as a function of time. Instead of fitting the decay curve into an exponential equation (black line in graph 201), the raw data (intensity at each pixel) is transformed into polar coordinates by plotting the sine (red line) and cosine (blue line) using Fourier transformation, for every pixel in the object, the fluorescence lifetime can be obtained as "phasor lifetime" Phasor graph 202 depicts an exemplary phasor fingerprint of pure intrinsic biomarkers of free nicotinamide adenine dinucleotide (NADH) in solution, bound NADH in the presence of lactate dehydrogenase, and a long lifetime species derived from lipid droplets. Given that the free form of NADH exhibits a compact structure with a low fluorescence quantum yield (q)=0.019) and a short lifetime of 0.4 ns and the extended form of NADH bound to lactate dehydrogenase with a much higher quantum yield ($\varphi$=0.099) with a longer fluorescence lifetime up to −3.4 ns, the lifetimes of these two states can be easily distinguished. Based on the law of phasor addition, any sample containing the combination signature of these three species will fall within the triangle joining the three phasors.

When FLIM is coupled with two-photon excitation microscopy, molecules are excited at longer wavelengths (with lower energy photons). This prevents photodamage and allows deeper imaging, resulting in superior image quality. Since endogenous molecules such as collagen, retinoids, flavins, folate and NADH are fluorescent in live cells, fluorescence lifetime data can be used to identify these intrinsic fluorescent species. The contributions from these different biochemical species are indicators of an embryo's biochemical property. In the disclosed approach, the fluorescent lifetime signal from integrated images is acquired, and the raw data is transformed using a Fourier transformation to yield the average arrival time of emitted photons in each pixel, represented by polar coordinates "g" and "s" in the transformation function (Graph C in FIG. 3, FIG. 2). This allows the data to be presented in a two-dimensional graphical representation of the lifetime distributions, known as the phasor plot, for each pixel in the FLIM image (see FIG. 2).

Development of qualitative and objective means for assessing embryo quality and viability that are safer and faster will provide significant advances in IVF and animal breeding facilities. There is a need for a faster, safer, and objective method to assess embryo quality, in order to improve outcomes in assisted reproductive technology (ART) for IVF and animal breeding. The present invention satisfies this need.

SUMMARY OF THE INVENTION

In one aspect, a system for determining the viability of an embryo comprises an imaging device, an excitation device configured to direct an excitation energy at an embryo, a controller communicatively connected to the imaging device and the excitation device, configured to drive the excitation device at an excitation frequency and collect images from the imaging device at an imaging frequency, a non-transitory computer-readable medium with instructions stored thereon, that when executed by a processor perform steps comprising acquiring a set of images from the imaging device, performing a Fourier Transformation on the set of images to generate a set of phasor coordinates, computing a D-trajectory of the phasor coordinates, computing a set of values of additional parameters from the set of images and the phasor coordinates, comparing the set of values to a set of stored values related to embryos of known viability, and calculating a viability index factor of the embryo from the set of values and the set of stored values.

In one embodiment, the excitation energy is laser light. In one embodiment, the system further comprises a heat blocker positioned between the excitation source and the embryo, configured to prevent excessive heating of the embryo by the excitation source. In one embodiment, the imaging device is a fluorescence lifetime imaging microscope. In one embodiment, the additional parameters are selected from the group consisting of coordinates for a center of mass g and s, second axial moments a and b after diagonalization, an angle of distribution from diagonalization, and a total number of pixels in the phasor plot from slices derived from the phasor coordinates. In one embodiment, the excitation frequency is about 20 MHz. In one embodiment, the imaging device has a plurality of taps, and the instructions comprise the step of acquiring multiple images from the imaging device simultaneously using the plurality of taps. In one embodiment, the imaging device comprises two taps.

In another aspect, a method of calculating an embryo viability index comprises the steps of exciting an embryo with an excitation energy from an excitation source at an excitation frequency, acquiring a set of images of the embryo from an imaging device, performing a Fourier Transformation on the set of images to generate a set of phasor coordinates, computing a D-trajectory of the phasor coordinates, computing a set of values of additional parameters from the set of images and the phasor coordinates, comparing the set of values to a set of stored values related to embryos of known viability, and calculating a viability index factor of the embryo from the set of values and the set of stored values. In one embodiment, a power density of the excitation energy is greater than about 1 mW/nm and less than about 3.5 mW/nm. In one embodiment, the excitation energy is laser light having a spectral range between 390 nm and 2000 nm. In one embodiment, the parameters are selected from the group consisting of coordinates for a center of mass g and s, second axial moments a and b after diagonalization, an angle of distribution from diagonalization, and a total number of pixels in the phasor plot from slices derived from the phasor coordinates.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION

Figure 1:
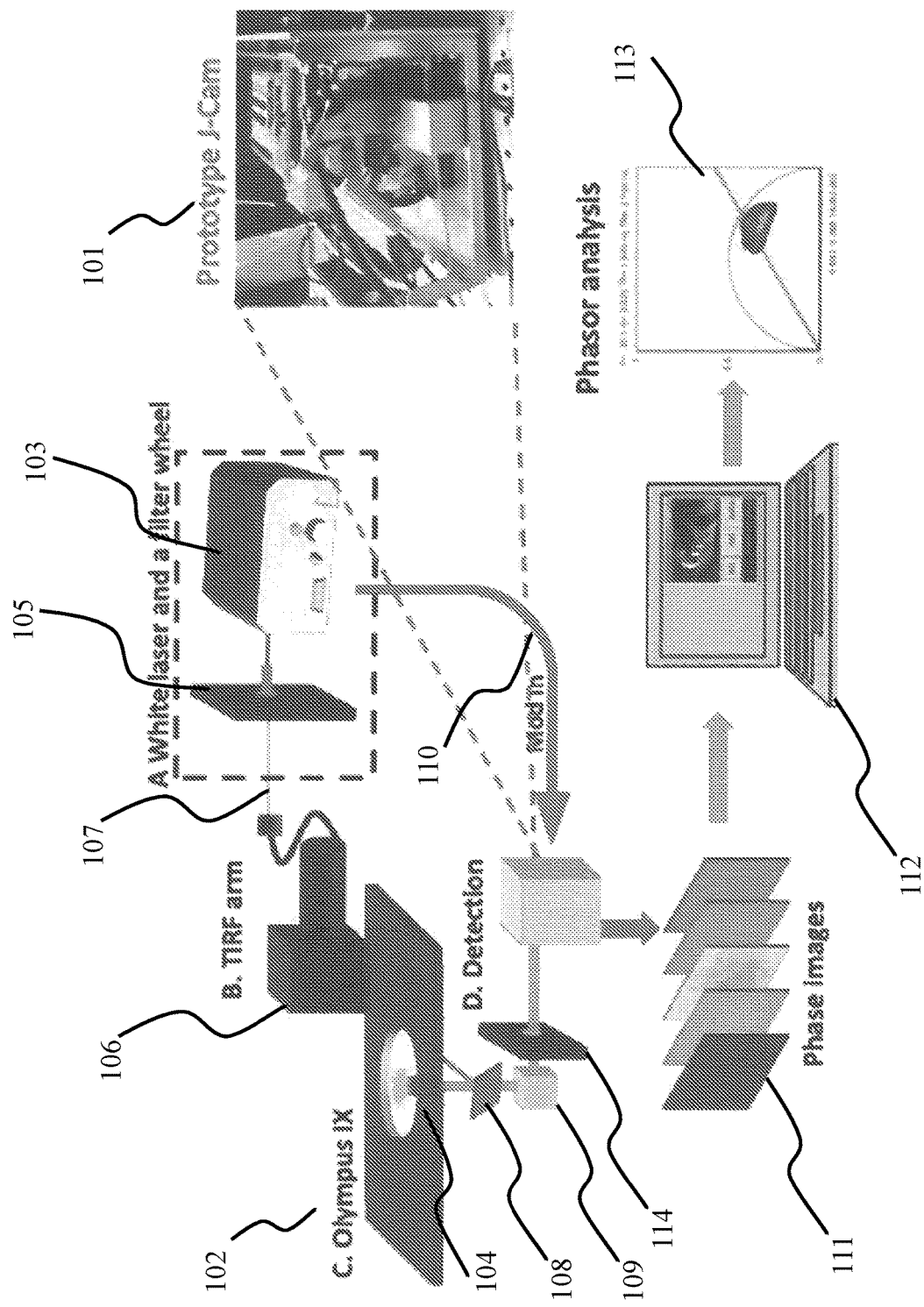
FIG. 1 is a schematic diagram of a system of the invention.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Although certain embodiments of systems and methods disclosed herein may be described in reference to determining embryo viability, it is understood that the systems and methods may be used for other processes, for example to determine properties of one or more cells, tissues, or living organisms more generally. Suitable examples include, but are not limited to, identifying changes in metabolism due to cell cycle, stress, cancer diabetes, and neurodegenerative diseases within cell, tissue, and/or blood samples.

Certain elements of the disclosed invention constitute improvements over prior published work, including Ma et al., Label-free assessment of pre-implantation embryo quality by the Fluorescence Lifetime Imaging Microscopy (FLIM)-phasor approach, https://www.biorxiv.org/content/early/2018/03/22/286682.full.pdf, Mar. 22, 2018; updated version of the same https://www.biorxiv.org/content/10.1101/286682v2, published online Apr. 21, 2018; final version published in *Scientific Reports* vol. 9, 13206 (Sep. 13, 2019); and Chen et al., Widefield multi-frequency fluorescence lifetime imaging using a two-tap complementary metal-oxide-semiconductor (CMOS) camera with lateral electric field charge modulators, Journal of biophotonics, Nov. 12, 2018; all of which are incorporated herein by reference.

A conceptual illustration of an imaging device of the present invention is shown in FIG. 1. An imaging device 101 is positioned to gather imaging data from a sample through microscope optics. The imaging device may in some embodiments comprise a CMOS camera, based on the lateral electric field charge modulator (LEFM) technique. In some embodiments, the imaging device may comprise one or more of a modulated CMOS camera, a charged coupled device (CCD), an electron-multiplying CCD (EMCCD), an intensified CCD, a photomultiplier tube (PMT), an avalanche photodiode (APD), or a single-photon avalanche diode (SPAD). It is understood that an "imaging device" as described herein could be any imaging device, including but not limited to a camera, a scanning device, a microscope, for example a fluorescence lifetime imaging microscope (FLIM), or a point detector.

The imaging device may be physically attached to a camera port of a microscope, or in some embodiments, all or part of the imaging device may be incorporated into a microscope. In the depicted example, the microscope is an Olympus TIRF microscope. An excitation source 103 is positioned to provide excitation and/or illumination to the sample 114—in the depicted example, the excitation source is a white-light supercontinuum laser (SC390, Fianium, Inc), but it is understood that any suitable excitation or illumination source could be used, including but not limited to lasers in different color regions, laser diodes, light emitting diodes (LEDs), photon lasers, photon excitation lasers, specific light sources, lamps, or multiphoton excitation sources. An excitation source may have a spectral range, for example a broad spectral range of between 390 nm to 2000 nm. In other embodiments, a narrower or more specific spectral range may be used, for example limited to certain color bands in the visible, ultraviolet, and/or infrared spectrum. Suitable exemplary spectral ranges include, but are not limited to, 380 nm to 740 nm, 450 nm to 980 nm, 500 nm to 740 nm, or any other suitable range or combination of ranges.

The excitation source may in some embodiments include or be used in conjunction with one or more filters or excitation cleaners, for example a filter wheel 105. Suitable filters include, but are not limited to, low-pass filters, high-pass filters, band-pass filters, heat blockers, filter wheels, or beam splitter glass. In one embodiment, a filter of eight band-pass filters is used. In some embodiments, the one or more filters are mounted on a movable device so that the filter or filters in the excitation path may be adjusted, manually or with a controller. In some embodiments, the controller includes one or more elements of computer control. In one embodiment, the power density of the excitation or illumination source may be >1 mW/nm. In some embodiments, the power density is between 1 µW/nm and 100 mW/nm, or between 100 µW/nm and 10 mW/nm, or between 1 mW/nm and 5 mW/nm. In other embodiments, the excitation source may be generated at an energy level in a range of between 25 µJ and 25 J, or between 50 µJ and 10 J, or between 100 µJ and 5 J, or between 1 mJ and 1 J, or between 10 mJ and 100 mJ, or between 2511.1 and 1 mJ, or between 5011.1 and 10 mJ, or between 100 mJ and 10 J, or between 1 J and 25 J, or between 10 J and 25 J.

An excitation cleaner 104 may in some embodiments be a heat blocker, which may be provided in the excitation path to reduce certain types on excitation energy from the excitation source from reaching the sample. In some embodiments, the excitation cleaner is an an infrared (IR) blocker. Although an IR blocker is used in certain exemplary embodiments described herein, any suitable excitation energy blocking material that is transparent to one or more wavelengths of light from the excitation source may be used.

A Total Internal Reflection Fluorescence (TIRF) element 106 may be used in conjunction with the excitation source and the microscope. In the exemplary embodiment of FIG. 1, the TIRF element 106 is an Olympus TIRF arm, which is connected to the excitation source 103 via fiber optic cable 107. After entering the microscope 102, the excitation beam may be reflected or diverted by one or more optic elements. In the depicted example of FIG. 1, the beam is diverted to a dichoric mirror 108, then through a prism 109, which diverted the beam to illuminate the sample 114, which was in turn imaged by imaging device 101. In some embodiments, a synchronization signal 110 may synchronize pulses or periodic excitation from a modulated excitation source 103 and image acquisition from an imaging device 101.

In some embodiments, excitation source 103 is a modulated excitation source having an excitation frequency, which may be synchronized with imaging device 101. Modulation frequencies for a device of the present invention include, but are not limited to any frequency suitable for use with fluorescence-lifetime imaging microscopy (FLIM), for example between 1 MHz and 1 GHz, or between 1 MHz and 200 MHz, or between 1 MHz and 100 MHz, or between 2 MHz and 80 MHz, or between 5 MHz and 50 MHz, or between 10 MHz and 30 MHz, or about MHz, or any other suitable modulation frequency range.

Synchronization and modulation of the excitation source and the imaging device may be controlled either by a controller connected to or integrated with the excitation source, or by a controller connected to or integrated with the imaging device. In some embodiments, the imaging device includes an embedded controller, for example a controller comprising a microcontroller, ASIC, and/or FPGA. An imaging device 101 of the present invention may have multiple "taps", to provide for accelerated readout of image data from the sensor by reading from multiple locations on the pixel sensor simultaneously. In some embodiments, an imaging device of the present invention may have one tap, two taps, four taps, eight taps, or more. In some embodiments, multiple imaging devices may be used, for example with a beam splitter or other image splitting device, in order to gather more image data from a sample at higher speeds.

Where multiple taps are used, the multiple taps may be acquired and combined based on the phase order in a period, i.e. in one full period measurement, two or more sets of phase images are actually acquired. The phase steps can be set according to the requirement of harmonics and imaging time. For example, if a high harmonic frequency, for example a 31 st harmonic (620 MHz), is needed, the phase steps can be set to 64. As a result, the FLIM imaging time is 64 frames. In some measurements, 16 phase steps are used as balance of harmonic contents and FLIM imaging speed. Images may be acquired via a computer-controlled image acquisition peripheral, for example a Framelink PCIe card (VCE-CLPCIe01, Imperx, USA). The maximum frame range of this camera is 12 fps. A USB connection may be used to connect the camera to the computer 112 containing the image acquisition peripheral, for example in order to send control signals or firmware to the imaging device. An embedded FPGA may be used in some embodiments to perform various operations, e.g. phase control and sweeping. Such a configuration greatly reduces the complexity required in daily operation. The acquired phase images 111 may then undergo further processing in an image processing software. In one embodiment, SimFCS software is used. All data may be graphically analyzed by a phasor method, which allows easy fit-free lifetime analysis of FLIM images.

A system of the present invention may involve a computing device configured to process a quantity of data with a machine learning algorithm. In one embodiment, a portion of data measured from embryos with known or later discerned viability metrics is used as a training set, while a second portion of data measured from embryos with known or later discerned viability metrics is used as a test set.

In one exemplary embodiment, the FLIM data collected from individual embryos are placed in either of two categories, the H (control/healthy group has FLIM signature from the embryos developed to the blastocyst stage) and UH (sample/unhealthy group has FLIM signature from the embryos arrested at compaction stage or even earlier). The distance algorithm can generate a "spectra" from the given (up to 24 parameters) of phasor FLIM distributions corresponding to individual embryos. In one embodiment, the 24 parameters include, but are not limited to, the 2 coordinates for the center of mass g and s, 2 second axial moments a and b after diagonalization, the angle of the distribution from the diagonalization and the total number of pixels in the phasor plot from the 4 slices of the 3D phasor histogram. For each parameter set, the average and standard deviation of the parameters was calculated. then a "distance" function was constructed in which the difference of the average of the two sets weighted by the variance of the parameter in each set for the group H and UH respectively was calculated.

Using distance analysis, a training set can be generated based on the best weight set that has been chosen to separate the H and UH set embryos according to the distance from the average of each set. In some embodiments, after the training set has been generated the rest of the embryos were tested, and an embryo viability index (EVI) is calculated for each embryo. Using the EVI index for the spectra of the training set, the data can be binned, for example into a histogram, in order to determine if a member is a true positive (below 0) or a false positive (above 0). Statistical methods such as the area under the curve (AUC) are then used to determine the quality of the training set. If the AUC is close to 1, the two groups are more separable since there are fewer false positives. More details of the distance analysis calculation can be found in Ranjit et al., Characterizing fibrosis in UUO mice model using multiparametric analysis of phasor distribution from FLIM images. Biomedical Optics Express 7, 3519-3530 (2016), incorporated herein by reference.

A method of the present invention applies the phasor-fluorescence lifetime imaging microscopy (FLIM) method and examines the dynamic endogenous biomarker changes during preimplantation embryo development. Based on the quantifiable physiological property changes, the biomarker changes are correlated to embryo viability (see FIG. 3). This non-invasive phasor-FLIM analysis is sensitive, quick and intuitive. When the disclosed method is applied to pre-implantation mouse embryos, detailed data was captured on their metabolic states at various developmental stages. At each stage, the mouse embryo displays a characteristic phasor-FLIM signature.

For the first time, the disclosed method defines a unique graphical metabolic trajectory that correlates with energy metabolism and embryo development, referred to herein as the developmental trajectory or "D-trajectory". Initially, embryos uptake pyruvate during glycolysis as their main energy source. As the embryos develop to later stages, the need for ATP increases in order to activate transcription for proliferation. Then, the embryos switch from glycolysis to oxidative phosphorylation, primarily using glucose as their energy source, which also changes the relative redox potential (NAD+: NADH ratio). The spectroscopic signatures from each of these changes are detected and can be used as criteria to identify healthy embryos at each stage in development. The D-trajectory of pre-implantation embryos cultured in nutrient-deficient media deviates significantly from that of those cultured in normal media, indicating that lifetime trajectories can be used to detect metabolic alterations in embryos. Methods of the present invention are able to calculate several different mathematical parameters that are statistically different between healthy and unhealthy pre-implantation embryos based on machine learning information. Therefore, methods of the present invention provide an objective, non-invasive, and quantitative method to assess the quality of mammalian embryos.

Figure 3:
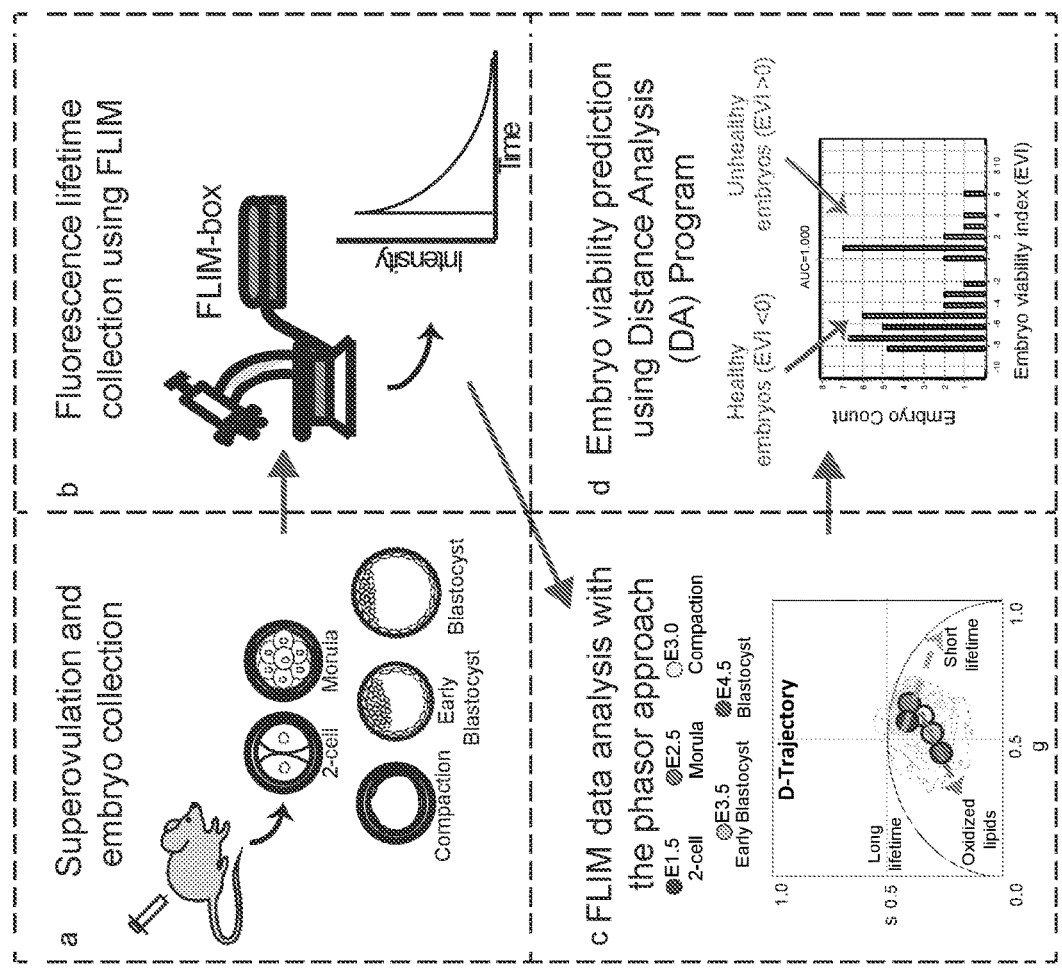
FIG. 3 is a diagram of a method of the invention.

With reference now to FIG. 3, an application of a non-invasive live imaging approach capable of measuring NADH levels within living mouse embryos undergoing in vitro culturing is shown. In step A, embryos are collected from pre-implantation stages. In step B, intrinsic fluorescence lifetimes are obtained for each embryo using a microscope coupled with a FLIM box. In step C, the data is analyzed with the phasor approach, and in step D, a distance analysis is conducted in order to predict embryo viability.

A phasor-FLIM approach is applied, and information is captured on metabolic energy sources (e.g., NADH) utilized by pre-implantation embryos. A phasor-FLIM signature of free- or bound-NADH changes dynamically as an embryo undergoes specific developmental stages. When oxidative phosphorylation is disrupted using complex I and III inhibitors, the phasor-FLIM signature is also significantly affected, suggesting that the phasor-FLIM approach is sensitive to the metabolic (free/bound) state of NADH in embryos. In some embodiments, methods of the present invention can be used to identify embryos in healthy conditions and in nutrient-lacking "high stress" conditions at a time period before such a morphological difference can be identified by an expert from a transgenic mouse facility. In one embodiment, the difference may be identified 24 hrs before it would be detected by such an expert.

Figure 4:
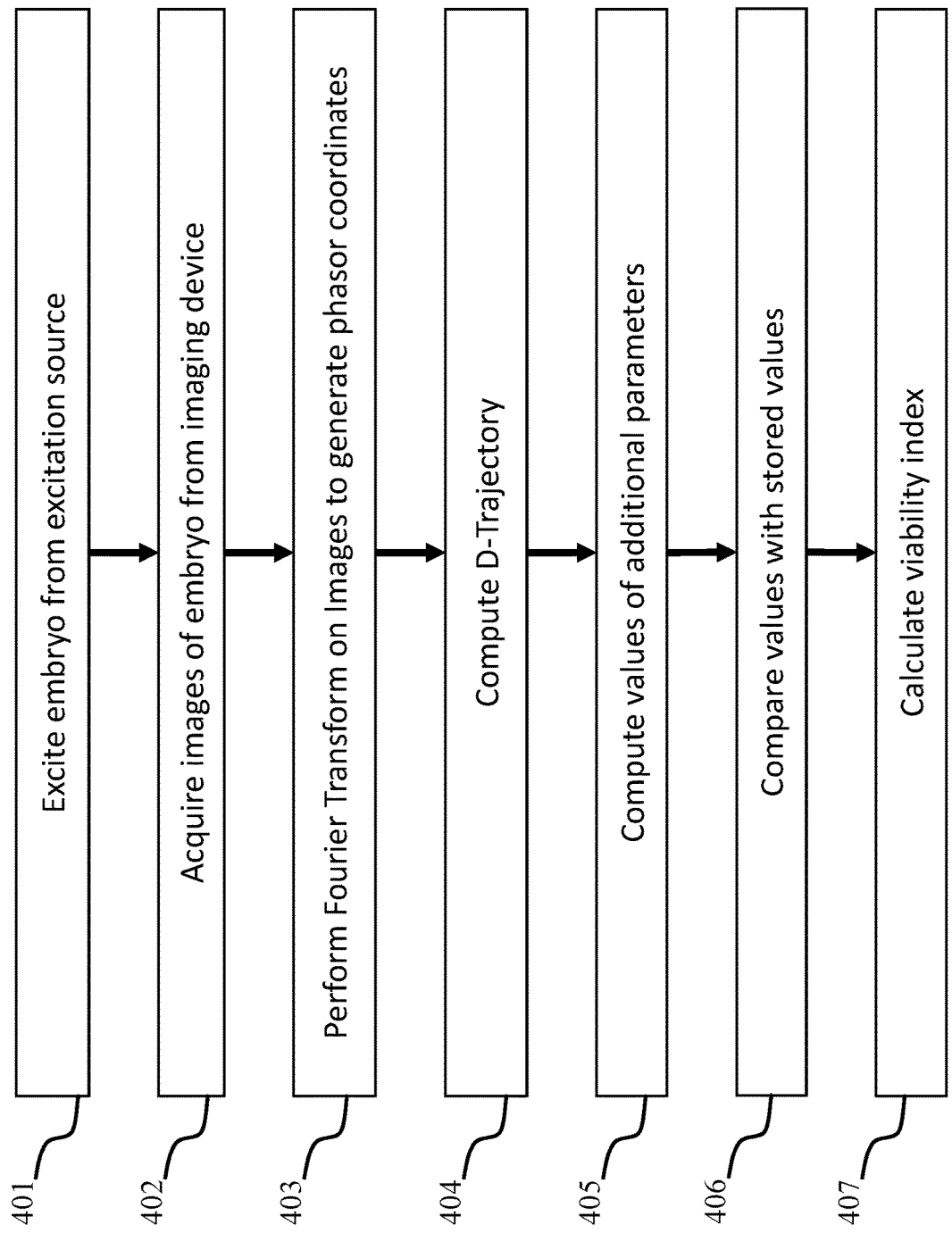
FIG. 4 is a method of the invention.

With reference to FIG. 4, a method of calculating an embryo viability index is shown. The method comprises the steps of exciting an embryo with an excitation energy from an excitation source at an excitation frequency in step 401, acquiring a set of images of the embryo from an imaging device in step 402, performing a Fourier Transformation on the set of images to generate a set of phasor coordinates in step 403, computing a D-trajectory of the phasor coordinates in step 404, computing a set of values of additional parameters from the set of images and the phasor coordinates in step 405, comparing the set of values to a set of stored values related to embryos of known viability in step 406, and calculating a viability index factor of the embryo from the set of values and the set of stored values in step 407.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the system and method of the present invention. The following working examples therefore, specifically point out the exemplary embodiments of the present invention, and are not to be construed as limiting in any way the remainder of the disclosure.

Safety

Figure 5A:
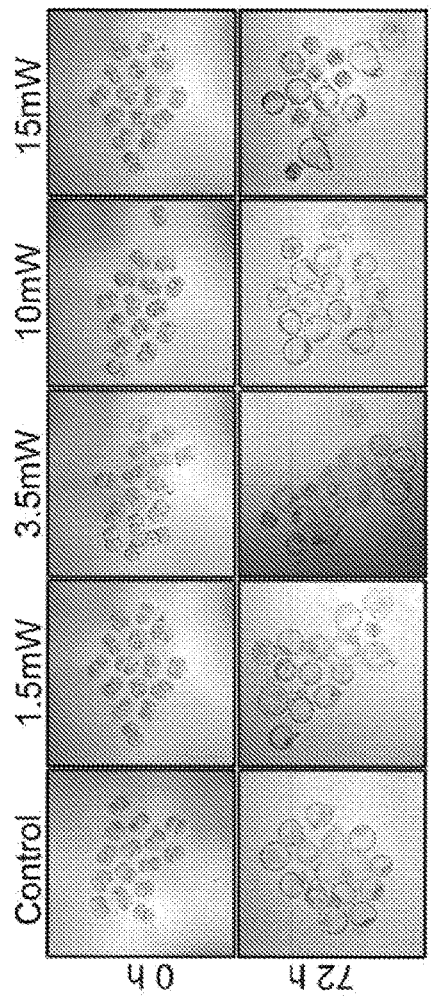
FIG. 5A is a set of images and graphs related to experimental data.
Figure 5A:
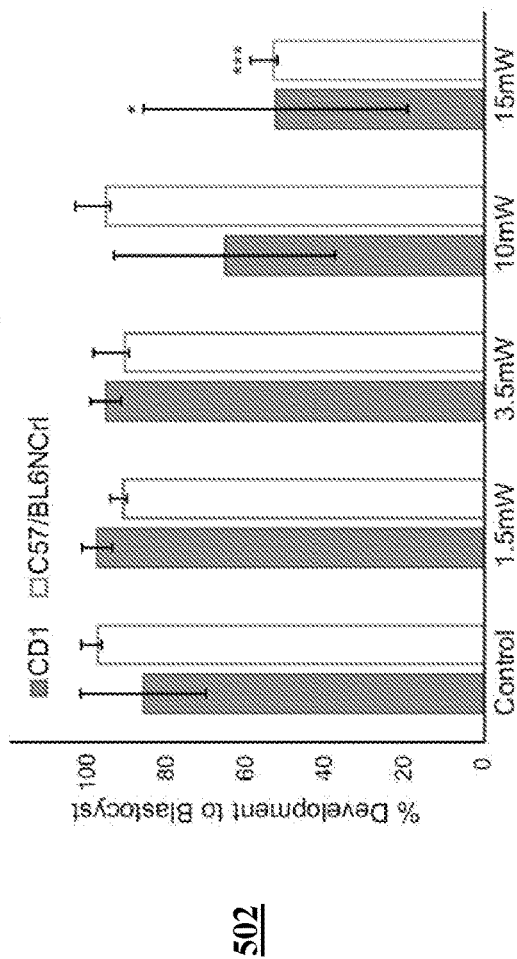
Figure 5B:
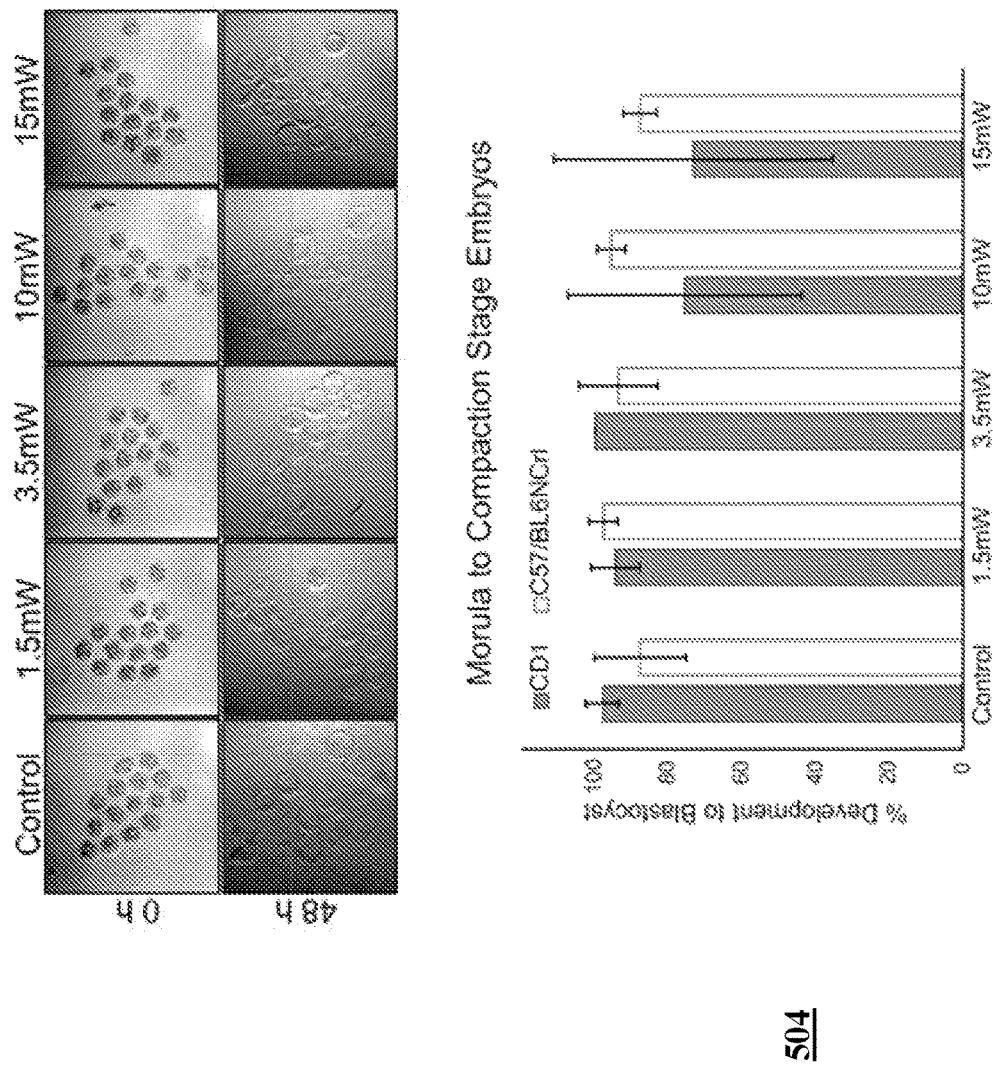
FIG. 5B is a set of images and graphs related to experimental data.

In order to ensure the safety of the FLIM imaged embryos, the optimum laser power to avoid DNA damage, while allowing the rapid and robust acquisition of the FLIM signal on mouse pre-implantation embryos was determined. 2-cell (E1.5) and morula (E2.5) stage CD1 and C57/BL6NCrl embryos were exposed to varying laser powers (1.5, 3.5, 10, and 15 mW) and the effect on the developmental progression of embryos until the blastocyst stage was examined (see FIG. 5A and FIG. 5B). With reference to FIG. 5A, images 501 depict transmission images of embryos before and after imaging and culturing for 72 hours till E4.5. Image size is 708.49*708.49 μm. Graph 502 shows an assessment of embryonic development after imaging and 72-hour in vitro culture reported as percent development. CD1: E1.5 non-imaged control (n=72); 1.5 mW (n=42); 3.5 mW (n=42), 10 mW (n=31), 15 mW (n=45) imaged embryos. C57BL/6NCrl: E1.5 non-imaged control (n=37); 1.5 mW (n=37); 3.5 mW (n=36), 10 mW (n=38), (n=37) imaged embryos.

In order to capture FLIM-signals of embryos taken with 1.5 mW laser power, 4 times longer exposure time was required than the embryos collected at 3.5 mW, 10 mW, 15 mW laser powers due to their low signal to noise ratio. The majority of embryos exposed to 1.5 mW and 3.5 mW laser power developed to the blastocyst and there were no significant differences between the control (non-imaged) and embryos imaged at the 2-4cell stage or morula-compaction stage, irrespective of strain differences (CD1 or C57BL/6NCrl) (see FIG. 5A and FIG. 5B). However, at 10 mW, approximately 20% and 35% of CD1 embryos imaged at the 2-cell and compaction stages, respectively, fail to progress to the blastocysts. At 15 mW, nearly 50% of CD1 and C57BL/6NCrl embryos imaged at the 2-cell stage were arrested before the compaction stage, while approximately 30% of CD1 and 12% of C57/BL6NCrl embryos imaged at the compaction stage failed to develop to blastocysts. It was concluded that CD1 embryos are more sensitive to laser damage, and that 3.5 mW is the ideal laser power for FLIM analysis.

Next, the activation of the DNA repair pathway in the embryo was examined by conducting immunofluorescence staining for anti-phosphorylated Histone 2AX (H2AXs139), a novel marker for DNA-double strand breaks. Both the non-imaged control and FLIM-imaged embryos were indistinguishable and did not show any signs of DNA repair pathway activation at 3.5 mW. However, embryos exposed to 1.5 mW laser power, which required longer laser exposure time (12 minutes, instead of ~3 minutes) showed the sign of DNA damage (see FIG. 5C).

Figure 5C:
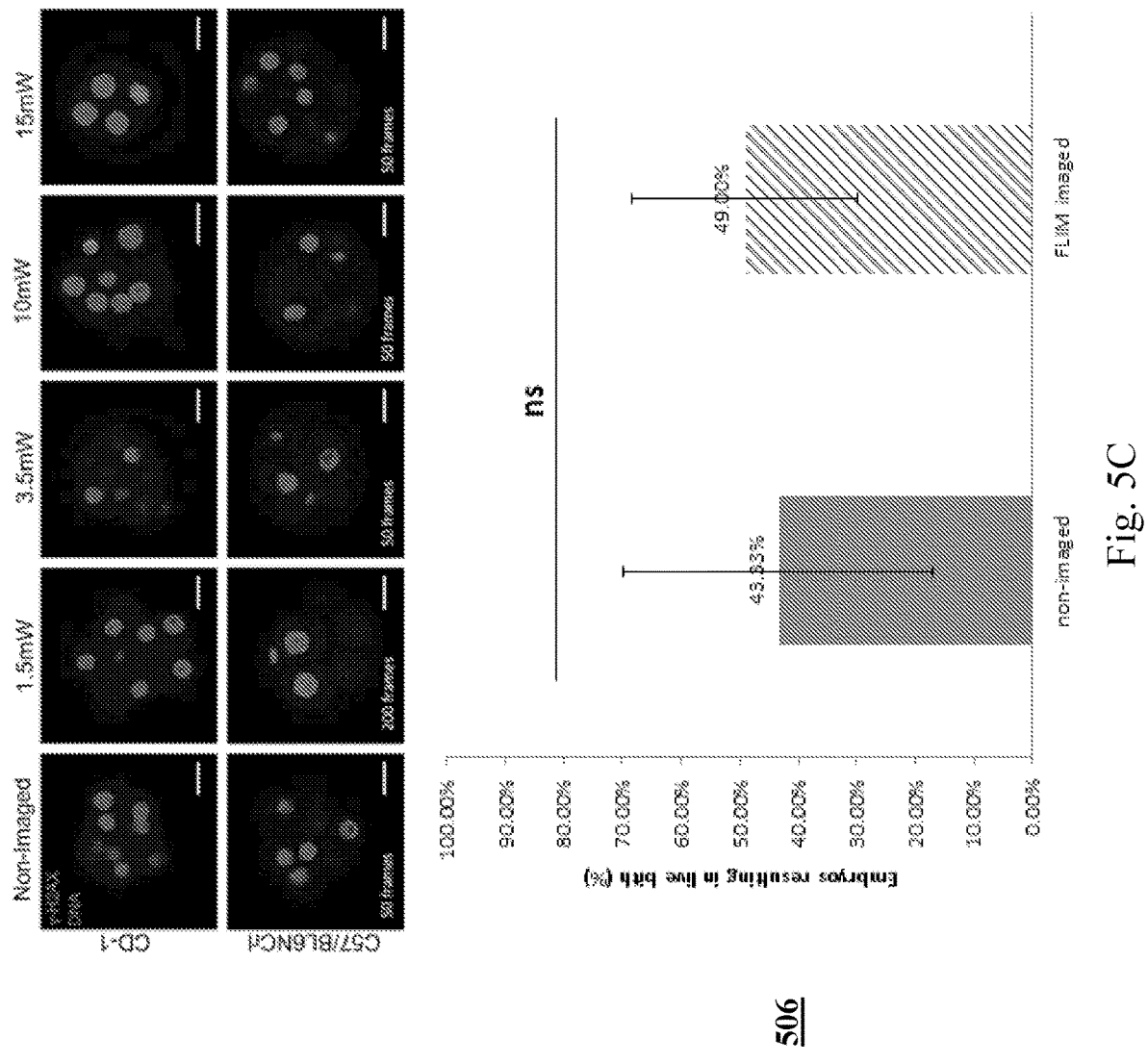
FIG. 5C is a set of images and graphs related to experimental data.

With reference now to FIG. 5C, images 505 depict H2AX staining of FLIM imaged pre-implantation embryos. Two strains of embryos were FLIM imaged at E.1.5 stage and subjected to Hoechst (blue) and H2AX (red) staining at E2.5 for DNA-damage assessment. Control: no FLIM FLIM-imaged embryos. For CD1: E2.5 control (n=3); 1.5 mW (n=3); 3.5 mW (n=3), 10 mW (n=3) and 15 mW (n=3). For C57/BL6NCrl: E2.5 control (n=9); 1.5 mW (n=9); 3.5 mW (n=8), 10 mW (n=6), and 15 mW (n=8). Scale bar set to 201 µm. Graph 506 shows live birth rates of FLIM-imaged embryos. Control (solid blue, n=88) and FLIM-imaged CD1 embryos (diagonal stripes, blue, n=94) were allowed to develop to blastocysts and implanted into 13 pseudo pregnant mice (3 independent trials). The pups were collected from C-section on E18.5. There is no difference for the live birth rate (p-value, 0.662).

Finally, the effects of FLIM on the rate of pregnancy were examined. Specifically, FLIM-imaged at E2.5 and control BRE-gal embryos were allowed to advance to early blastocyst stage (E3.5) and 12-16 control and FLIM-imaged embryos were implanted per pseudopregnant mother split evenly between the left and right uterine horn. E18.5 embryos were collected through caesarean section (C-section) and counted for implantation efficiency (Graph 506 and Table 1, Table 2, and Table 3, below). The average live birth rates were 49% for FLIM-imaged group and 43% for the non-imaged BRE-gal control group based on three independent experiments (Table 1, Table 2, and Table 3). Student t-test reveals that there is no significant statistical difference between FLIM-imaged and non-imaged groups. It was therefore concluded that FLIM imaging of the morula stage embryo at 3.5 mW excitation is safe to use and employed in the subsequent experiments.

TABLE 1

|  | CD-1 Embryos Implanted | BRE-gal$^{+/-}$ Embryos Implanted | CD-1 E18.5 | BRE-gal$^{+/-}$ E18.5 |
| --- | --- | --- | --- | --- |
| Trial 0 | | | | |
| Mice 1 | 7 | 7 | 5/7 (71.4%) | 4/7 (57.1%) |
| Mice 2 | 7 | 7 | 1/7 (14.3%) | 1/7 (14.3%) |
| Mice 3 | 7 | 7 | 4/7 (50%) | 2/7 (25%) |
| Mice 4 | 7 | 7 | 1/7 (12.5%) | 4/7 (50%) |
| Total | 28 | 28 | 11/28 (39.3%) | 11/28 (39.3%) |
| Trial 1 | | | | |
| Control 1 | 8 | 8 | 4/8 (50%) | 6/8 (75%) |
| Imaged 1 | 8 | 8 | 6/8 (75%) | 2/8 (25%) |
| Imaged 2 | 8 | 8 | 2/8 (25%) | 6/8 (75%) |
| Imaged 3 | 8 | 8 | 1/8 (12.5%) | 2/8 (25%) |
| Imaged 4 | 8 | 8 | 4/8 (50%) | 4/8 (50%) |
| Total Control | 8 | 8 | 4/8 (50%) | 6/8 (75%) |
| Total Imaged | 32 | 32 | 13/32 (40.6%) | 14/32 (43.8%) |

TABLE 2

|  | CD-1 Embryos Implanted | BRE-gal$^{+/-}$ Embryos Implanted | CD-1 E18.5 | BRE-gal$^{+/-}$ E18.5 |
| --- | --- | --- | --- | --- |
| Trial 2 | | | | |
| Control 1 | 10 | 2 | 1/10 (10%) | 1/2 (50%) |
| Control 2 | 10 | 2 | 1/10 (10%) | 0/2 (0%) |
| Control 3 | 10 | 2 | 5/10 (50%) | 1/2 (50%) |
| Imaged 1 | 10 | 2 | 5/10 (50%) | 2/2 (100%) |
| Imaged 2 | 10 | 2 | 5/10 (50%) | 0/2 (0%) |
| Total Control | 30 | 6 | 7/30 (23.3%) | 2/6 (33.3%) |
| Total Imaged | 20 | 4 | 10/20 (50%) | 2/4 (50%) |

TABLE 3

|  | CD-1 Embryos Implanted | Bre-gal$^{+/-}$ Embryos Implanted | CD-1 E18.5 | Bre-gal$^{+/-}$ E18.5 |
| --- | --- | --- | --- | --- |
| Trial 3 | | | | |
| Control 1 | 14 | NA | 12/14 (85.7%) | NA |
| Control 2 | 14 | NA | 3/14 (21.4%) | NA |
| Control 3 | 14 | NA | 6/14 (42.9%) | NA |
| Imaged 1 | 14 | NA | 8/14 (57.1%) | NA |
| Imaged 2 | 14 | NA | 9/14 (64.3%) | NA |
| Imaged 3 | 14 | NA | 8/14 (57.1%) | NA |
| Total Control | 42 | NA | 21/42 (50%) | NA |
| Total Imaged | 42 | NA | 25/42 (59.5%) | NA |

Pre-Implantation Mouse Embryo Collection

Females at 21-24 days old were superovulated with pregnant mare serum gonadotropin (PMSG, Sigma) and 48 hours later with human chorionic gonadotropin (HCG, Sigma). Matings were set each evening after hCG injections. The following morning a vaginal plug was considered 0.5 days post fertilization and embryos were collected at desired stages by flushing oviducts or uterine horns. For time course collection (intrinsic fluorescence FLIM and THG measurements) superovulation and matings were staggered and all the embryos were collected the same day except late blastocysts (E4.5) were generated by dissecting at E3.5 (one day before imaging) and cultured till next day.

Embryo Culture

Embryos were cultured at 12.8% for hypoxia condition or 20.9% $O_2$ (measured using Neofox oxygen sensor), with 5%

$CO_2$ in nitrogen balance at 37° C. The drop size used was on average ~10 embryos/20 µl drop (1 drop per dish) except for the prediction test, where the drop size was on average 1 embryo/3 µl drop (~10 drops/dish). Embryos were cultured and imaged on Matek Glassbottom Dishes (P35G-1.5-14-C). Single embryo cultures were used for embryo viability prediction (of 1 embryo per 3 µl of KSOMaa) to prevent the mobility of embryos and provide stable environment, to avoid ROS accumulation or influence of neighboring embryos, and to create a library for prediction and embryonic developmental potential. All other experiments were performed on group cultures ~10 embryos/20 µl drop (1 drop per dish). A 3D segmentation pipeline was used (see e.g. Chiang et al., Analysis of in vivo single cell behavior by high throughput, human-in-the-loop segmentation of three-dimensional images. BMC Bioinformatics 16, 397 (2015), incorporated herein by reference) to do a 3D reconstruction of embryos and conduct cell number analysis.

Inhibition of Oxidative Phosphorylation and Glycolysis:

Embryos were placed in 25 µl microdroplets of KSOMaa (Invitrogen) with the appropriate inhibitors covered in mineral oil (Sigma). Both of the two chemical inhibitors, rotenone and antimycin A cocktail (R&A) and 2-Deoxyglucose (2DeoxyG) were dissolved in KSOMaa. For R&A, the inhibitor was prepared to perform dose dependence measurements for a final concentration of 100 nM and 500 nM. For 2DeoxyG, the inhibitor has a final concentration of 1 mM. KSOMaa was used as a solvent and culture media for the control group and treatment group embryos.

H2AXs139 Staining

CD1 and C57BL/6NCrl post-imaged embryos are rinsed with Tyrode's acid (Sigma) 3 times and placed in holding and flushing media for 5 minutes to allow embryos to acclimate before 30-minute fixation in 4% paraformaldehyde on ice. Embryos were permeabilized using Triton X-100 (Fisher). And then embryos were incubated with H2AXs139 (Genetex) at 1:1000 for 1 hour at room temperature. Embryos were rinsed in 1× PBT three times and then stained with AlexaFluor555 at 1:200. Embryos were rinsed in 1×PBS three times before processing for the Hoechst (Sigma) staining for 10 minutes to stain the DNA. Finally, embryos were rinsed and imaged in 1×PBS using 780 Zeiss microscope and Zen 2012 software.

Embryo Implantation and C-Section at E18.5

CD-1 female mice were mated with vasectomized males to generate pseudopregnant females timed to E3.5 for implantation. E2.5 embryos were collected and imaged and implanted at E3.5. In each experiment, embryos were randomized before imaging to non-imaged and FLIM-imaged groups. After imaging, non-imaged embryos and FLIM-imaged embryos were randomized. The technician transferring the embryos was blinded to which embryos were imaged or nonimaged. 12-16 embryos were implanted into the left and right uterine horn of pseudopregnant females. E18.5 embryos were collected through C-section and counted for the implantation efficiency. Genotyping was done for experiments that used BRE-gal +/− embryos to differentiate between WT embryos to BRE-gal +/− embryos. Embryos were genotyped with Tissue Direct Phire PCR Kit with the following primers: (LacZ band) Fwd: 5' ATG AGC GTG GTG GTT ATG C 3' (SEQ ID NO:1), Rev: 5' GAT GGT TCG GAT AAT GCG 3' (SEQ ID NO:2); (Hprt band) Fwd: 5' AAG CCT AAG ATG AGC GCA AG 3' (SEQ ID NO:3), Rev: 5' AAG CGA CAA TCT ACC AGA GG 3' (SEQ ID NO:4).

DCF-DA Staining

Embryos were rinsed in Acid Tyrode 3×, washed in KSOMaa 3×, transferred to 5 uM DCF-DA in 1× PBS. Embryos were incubated in DCF-DA solution for 25 min at 5% $CO_2$ and 37° C. Embryos were then transferred to Hoechst stain solution for 8 min. Then embryos were placed in KSOMaa and imaged with LSM780 at 5% $CO_2$ at 37° C.

Fluorescence lifetime imaging microscopy (FLIM)

Fluorescence lifetime images of the pre-implantation embryos were acquired on Zeiss LSM710 (Carl Zeiss, Jena, Germany), a multi-photon microscope coupled with a Ti: Sapphire laser (Spectra-Physics Mai Tai, Mountain View, CA) with 80 MHz repetition rate. The FLIM data detection was performed by the photomultiplier tube (H7422p-40, Hamamatsu, Japan) and a320 FastFLIM FLIMbox (ISS, Champaign, IL). The pre-implantation mouse embryos were excited at 740 nm; an average power of ~3.5 mW was used. A Zeiss EC Plan-Neofluar 20×/0.5 NA objective (Cart Zeiss, Jena, Germany) was used. The following settings were used for the FLIM data collection: image size of 256×256 pixels, scan speed of 25.21 µs/pixel. A dichroic filter at 690 nm was used to separate the fluorescence signal from the laser light. And the emission signal was split with 496 nm LP filter and detected in two channels using a band pass filter 460/80 and a 540/50 filter. Every FLIM image was acquired for 50 frames of the same field of view with 256×256 per frame. Only the blue channel (460/80) data was used for this study. FLIM calibration of the system was performed by measuring the known lifetime of a fluorophore coumarin 6 (dissolved in ethanol), which has a known fluorescence lifetime of T=2.5 ns(37, 38). Embryos were kept in standard culture conditions, 37° C. and at 5% $CO_2$. FLIM data were acquired and processed by the SimFCS software developed at the Laboratory of Fluorescence Dynamics (LFD).

Figure 6A:
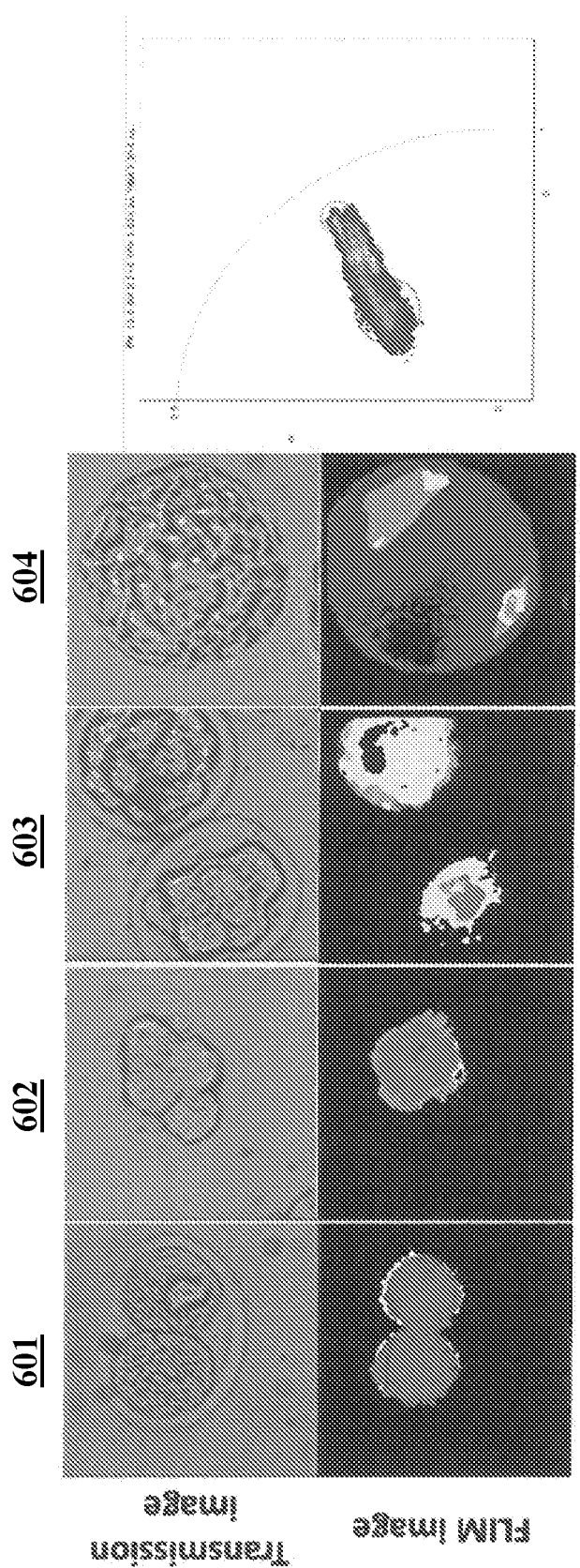
FIG. 6A is a set of transmission and FLIM images related to experimental data.

FLIM information was gathered with the prototype as shown in FIG. 1. The FLIM signature indicates the same trend as the previous literature reported, from glycolysis to oxidative phosphorylation during pre-implantation embryonic development. As shown in FIG. 6A, the transmission image and the correlated FLIM images of the pre-implantation embryos from E1.5 (2-cell, 601), E25 (compacting 8-cell stage, 602), E3.0 (morula, 603), and E4.5 (late blastocyst, 604) stage.

Figure 6B:
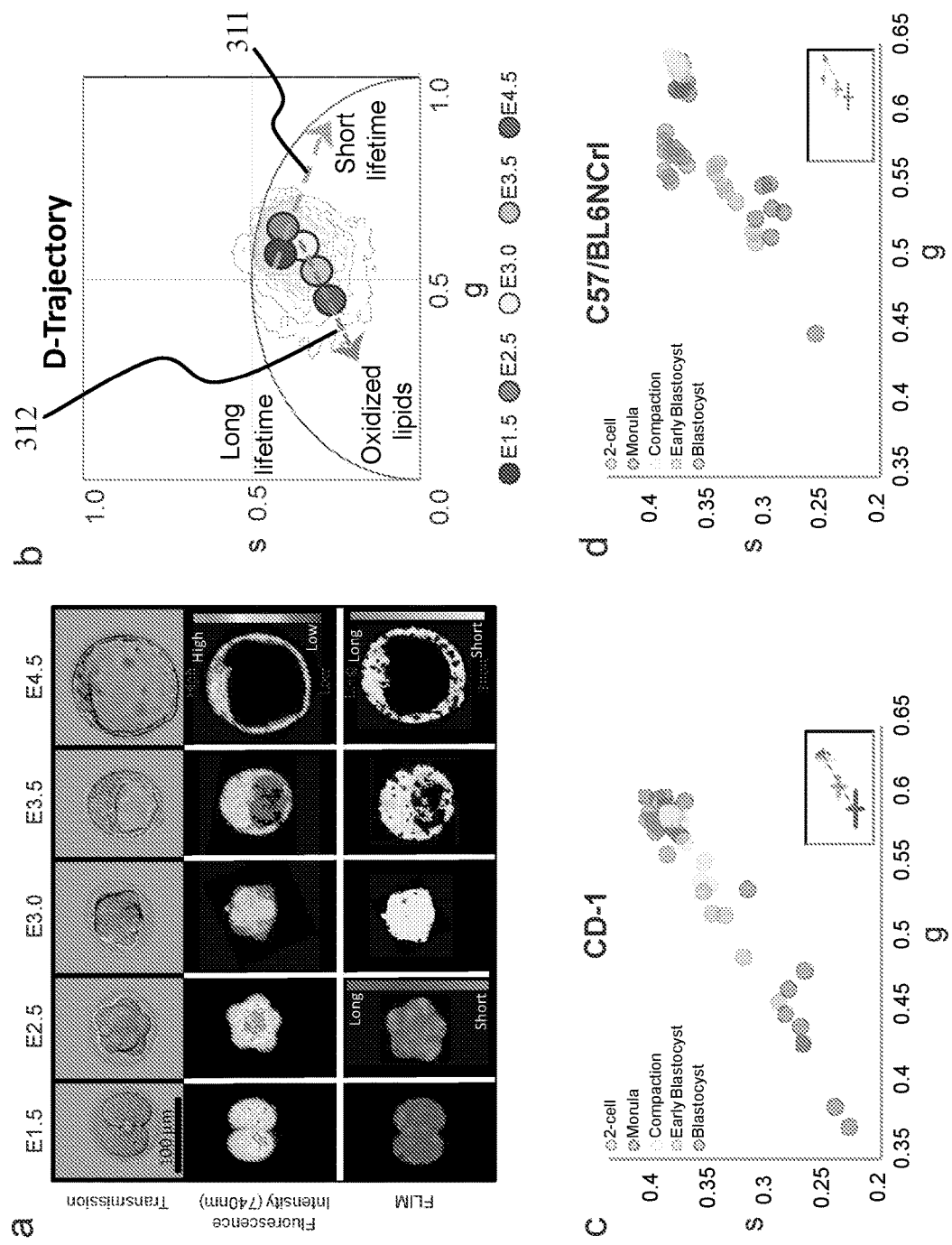
FIG. 6B is a set of FLIM images and graphs related to experimental data.

Additional data is shown in FIG. 6B. FIG. 6B shows how the lifetime trajectory of pre-implantation embryos correlates with embryonic development. The images A in FIG. 6B are Transmission (top row), fluorescence intensity (middle row, 740 nm excitation) and FLIM (bottom row) images of representative pre-implantation CD1 mouse embryos at 2-cell (E1.5), morula (E2.5), compaction (E3.0), early blastocyst (E3.5), and blastocyst stage (E4.5). In the FLIM images, the pseudo color displays the fluorescence lifetime. Phasor-plot B depicts average fluorescence lifetime of CD1 embryos at the indicated developmental stages demonstrating the D-trajectory (D for development). Arrow 611 indicates the fluorescence lifetime change from E1.5 to E2.5 and arrow 612 shows the change from E3.0 to E4.5. (C-D) Scatter plots show the D-trajectory for CD1 and C57BL/6NCrl embryos. The small window shows the average and standard deviation of each stage. CD1: 2-cell (n=29), morula (n=11), compaction (n=33), early blastocyst (n=50) and blastocyst stage (n=35); C57BL/6NCrl: 2-cell (n=25), morula (n=22), compaction (n=21), early blastocyst (n=38) and blastocyst stage (n=42). Graph C shows the D-trajectory of CD1 embryos (2-cell, n=8; morula, n=8; compaction, n=12; early blastocyst, n=5; blastocyst, n=8. and graph D shows the D-trajectory of C57BL/6NCrl embryos (2-cell, n=12; morula, n=11; compaction, n=9, early blastocyst, n=8; blastocyst, n=7). N=number of embryos analyzed.

Figure 7A:
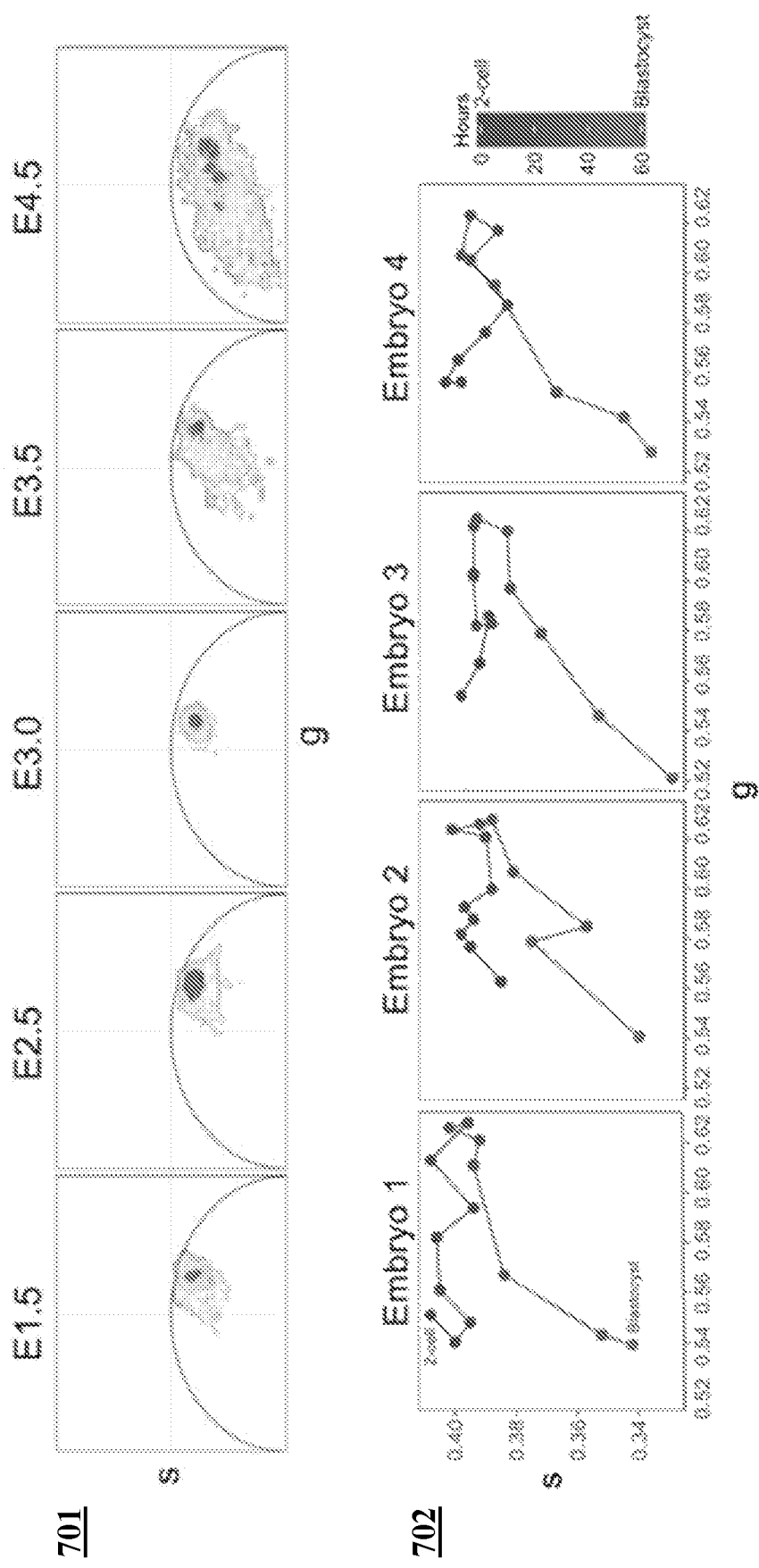
FIG. 7A is a set of phasor and scatter plots related to experimental data.

Two different mouse strains (a non-inbred CD1 and an inbred C57BL/6NCrl) were used to acquire a comprehensive representation of the phasor-FLIM distribution patterns of embryos during pre-implantation development (FIG. 6B and 701 in FIG. 7A). With reference to FIG. 6B, fluorescent lifetimes of endogenous fluorescent species, excited at 740 nm, were collected at the 2-cell (E1.5), morula (E2.5), compaction (E3.0), early blastocyst (E3.5) and blastocyst stage (E4.5), and pseudo-colored according to the phasor coordinates (A and B in FIG. 6B). The phasor coordinates, which is the averaged fluorescent lifetime, of the 2-cell and morula stage embryos have a unique lifetime distribution pattern distinct from all other cell and tissue types measured (arrow 611). This unique phasor lifetime position may reflect special characteristics of totipotent cells, which mirror low oxygen consumption and preferential utilization of pyruvate oxidation (see e.g. Shyh-Chang et al., Stem cell metabolism in tissue development and aging. Development 140, 2535-2547 (2013), incorporated herein by reference). On the other hand, compaction to blastocyst stages display average phasor coordinates typically observed in pluripotent cells (arrow 612) (see e.g. Stringari et al., Label-free separation of human embryonic stem cells and their differentiating progenies by phasor fluorescence lifetime microscopy. J Biomed Opt 17, 046012 (2012), incorporated herein by reference). This characteristic developmental time course lifetime distribution pattern is referred to herein as the developmental trajectory or "D-trajectory". Phasor-FLIM lifetime distributions of individual embryos from both outbred and inbred mouse strains, shown in graphs C and D in FIG. 6B, follow the similar developmental trend D-trajectory. In order to examine whether the genetic background of mice influences the D-trajectory, the trajectories of both CD1 and C57BL/6NCrl strains were compared (see graphs C and D in FIG. 6B). While the average lifetimes (g and s values) at specific embryonic stages are somewhat variable, the overall D-trajectory distribution (arrows 611 and 612) of C57BL/6NCrl is similar to that of CD1 mice. It follows that the D-trajectory is a characteristic distribution behavior observed among pre-implantation mouse embryos. In addition, time-lapse FLIM imaging was applied to individual embryos (n=16), and continuously followed at 3-hour time intervals from 2-cell (E1.5) to blastocyst stage (E4.5) for approximately 60 hours. The in vitro developmental trajectory (Graphs 702 in FIG. 7A) of each embryo mirrors the D-trajectory (Element B of FIG. 6B). Lastly, the phasor-FLIM developmental patterns were compared between the pre-implantation embryos cultured under ambient (20.9% oxygen) and oxygen-hypoxia condition (12.8% oxygen, trigas of 5% O2, 5% CO2, 90% N2 mixed with atmosphere) (703 in FIG. 7B). After 4 hours of incubation, the 2-cell (E1.5), morula (E2.5), compaction (E3.0), early blastocyst (E3.5) and blastocyst stage (E4.5) embryos were subjected to FLIM collection of endogenous fluorescent species, excited at 740 nm. The D-trajectories of embryos were similar between embryos grown under the ambient and hypoxic condition (arrows 611 and 612). The arrows were observed to shift slightly towards the right for the hypoxic condition, presumably due to the higher glycolysis rate. The shifts for the s and g coordinates are not significant. In sum, two combined lifetime trajectories (arrows 611 and 612) encompass the overall D-trajectory for normal pre-implantation embryo development.

Figure 7B:
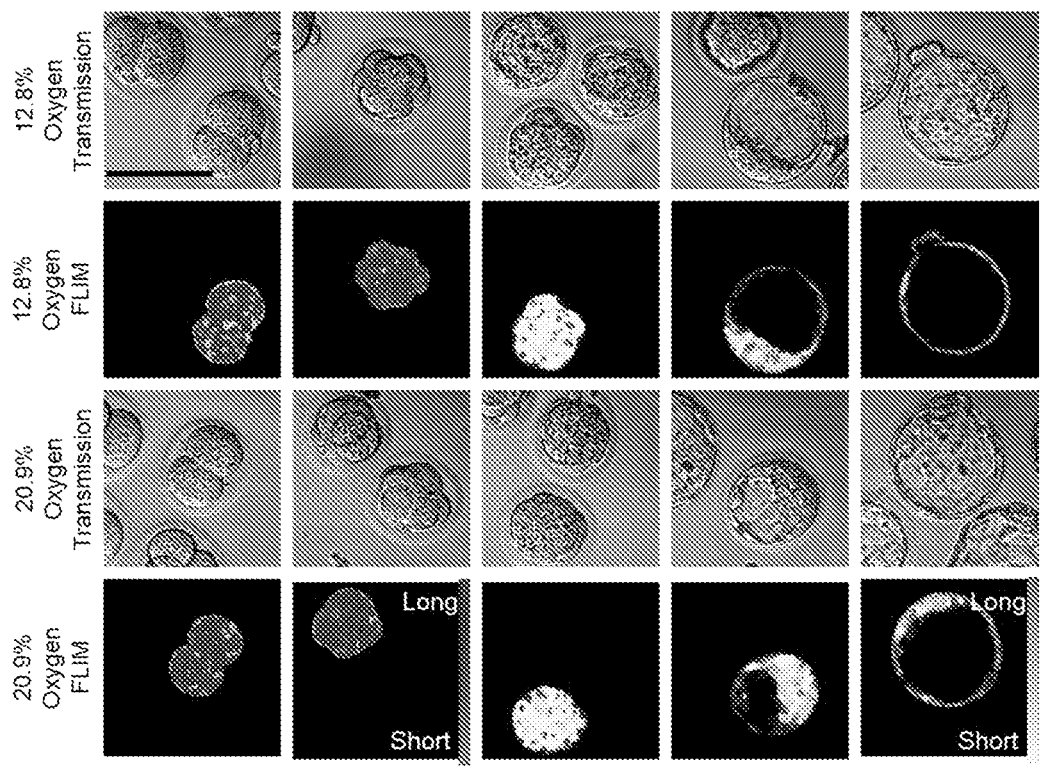
FIG. 7B is a set of images and graphs related to experimental data.
Figure 7B:
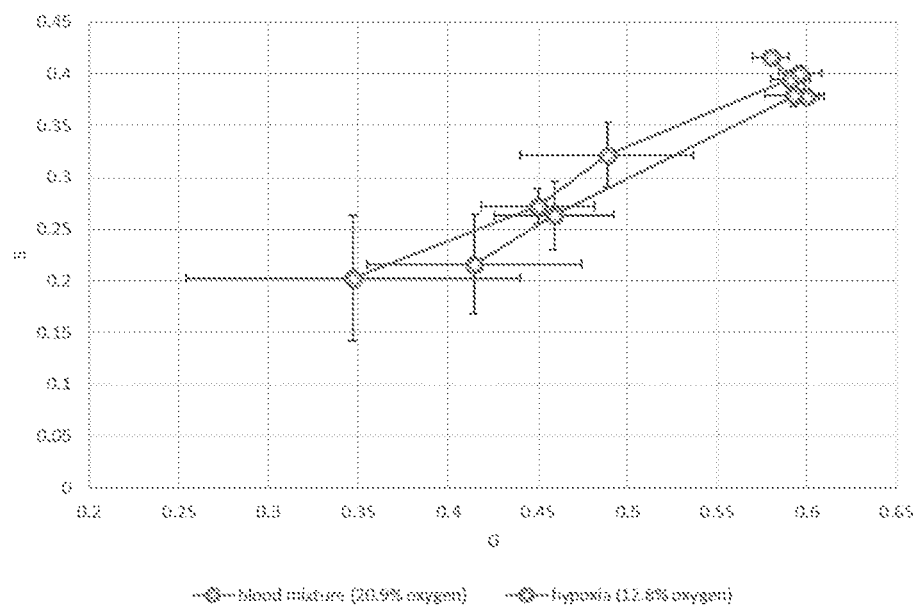

With reference to FIG. 7A, a development trajectory composed of two different trajectories that correlate with the metabolism of embryonic stages. Graphs 701 are representative phasor plots for the pre-implantation mouse embryo from early cleavage stage to blastocyst stage (E1.5-E4.5). Graphs 702 show four examples of the D-Trajectory observed throughout pre-implantation stages (from 2-cell to blastocyst stages). With reference to FIG. 7B, FLIM trajectories of embryos grown under ambient and hypoxic oxygen conditions are shown. Images 703 are transmission and FLIM images plots for the pre-implantation mouse embryo from early cleavage stage to blastocyst stage under 12.8% oxygen and 20.9% oxygen conditions. Graph 704 is a D-Trajectory showing the same trend for hypoxia condition (12.8% Oxygen, red) (n=19, 16, 11, 15, 13 for E1.5, E2.5, E3, E3.5, E4.5 stage respectively) and regular blood mixture culture condition (20.9% oxygen, blue) (n=29, 8, 11, 14, 11 for E1.5, E2.5, E3, E3.5, E4.5 stage, respectively). The straight lines show the developmental pattern of the embryos. The starting scatter is the top one for both groups represents E1.5. The last scatter of the lines is the left one for both groups represent E4.5. For g values of hypoxia treatment group, compare with regular blood mixture treatment group, p-value=0.296, 0.018, 0.829, 0.488, 0.584 for E1.5, E2.5, E3, E3.5, E4.5 stage, respectively (student t-test, two-tail test for g). The error bars show the standard deviation for each condition. Scale bar set to 100 μm.

Figure 2:
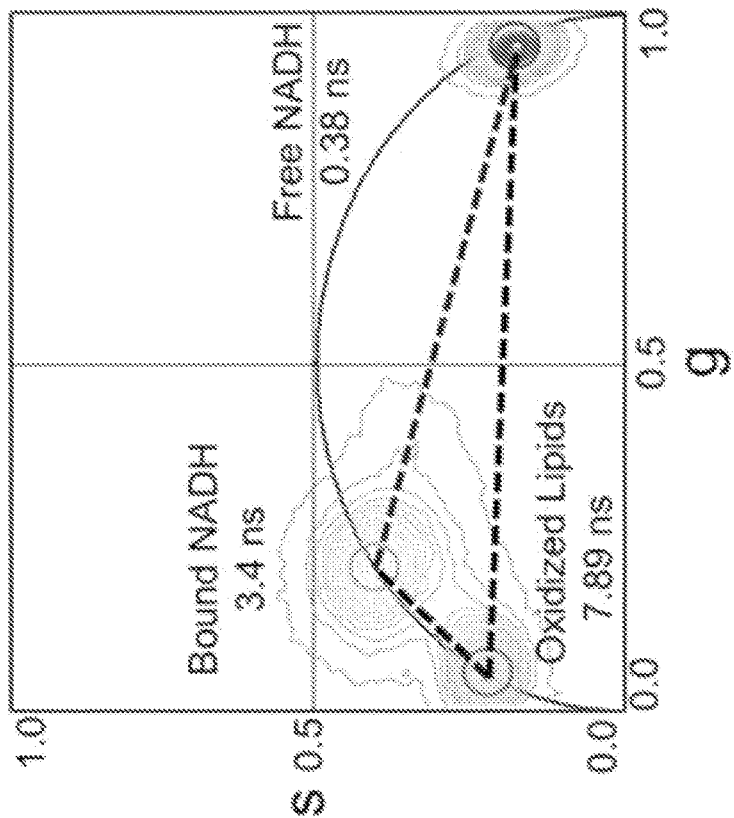
FIG. 2 is an illustrative example of a phasor transformation.
Figure 2:
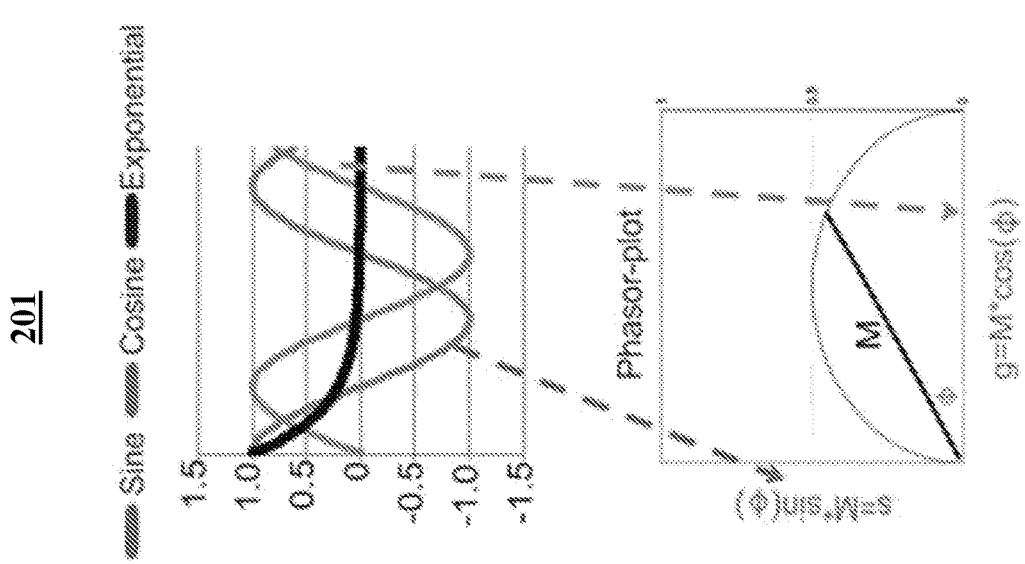
Figure 8:
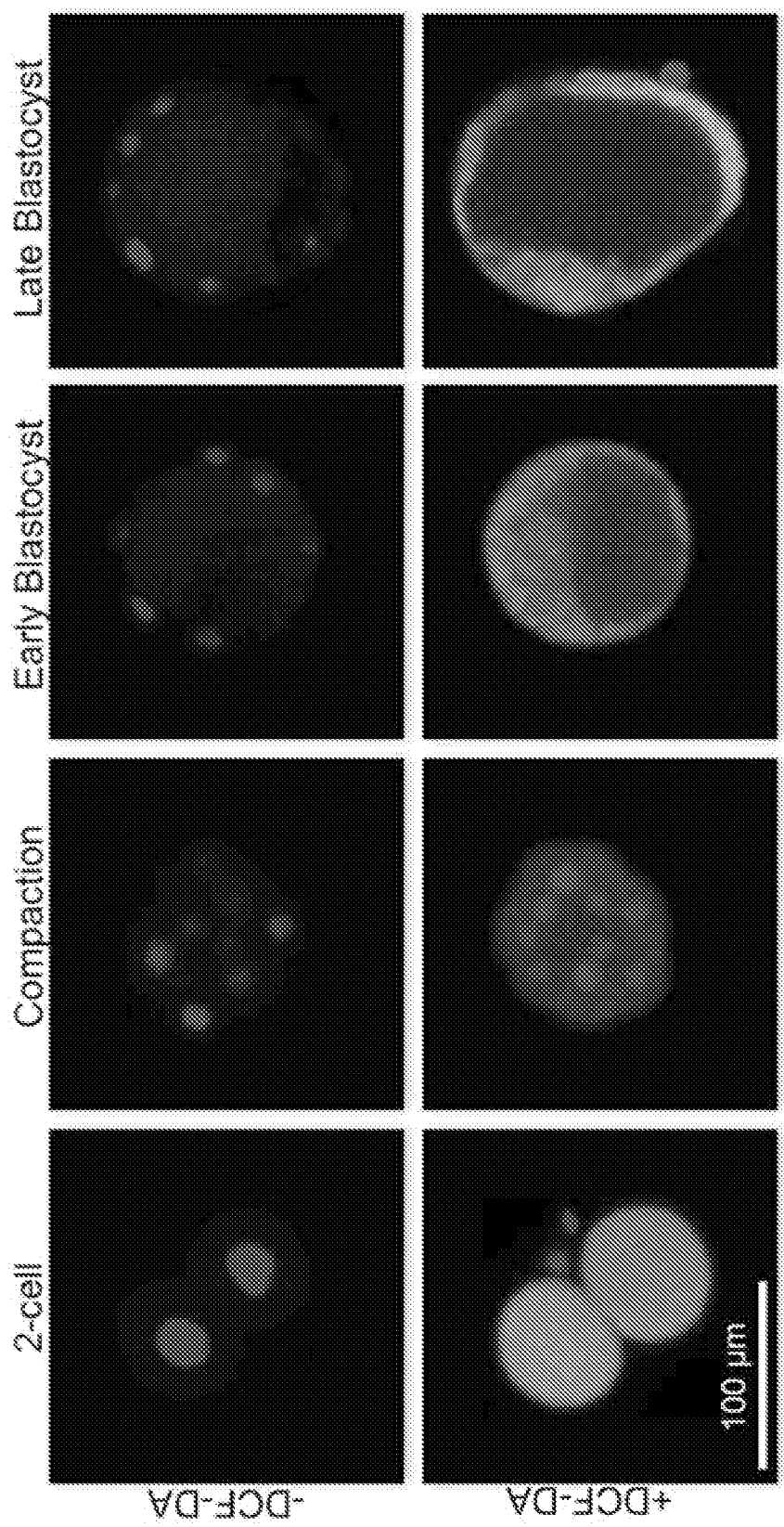
FIG. 8 is a set of images related to experimental data.

Reactive oxygen species (ROS) play a key role in cellular metabolism and homeostasis and ROS production has been linked to an increase in oxidized lipids. Arrow 612 in the D-trajectory is presumably due to an increasing fractional contribution of ROS as well as the oxidized lipids which have a fluorescence lifetime distribution of 7.89 ns and fall on the same published location (coordinates) of the semicircle in the phasor plot (see 202 in FIG. 2). This behavior is consistent with the model that an increase in aerobic respiration and metabolism as well as (3-oxidation during pre-implantation mouse development requires more efficient energy production from oxidative phosphorylation. The disclosed experiments confirm the presence of active ROS production with fluorogenic marker 2', 7'-dichlorofluorescin diacetate (DCF-DA, also known as H2DCFDA) staining (see FIG. 8).

Third-Harmonic Microscopy

Figure 9:
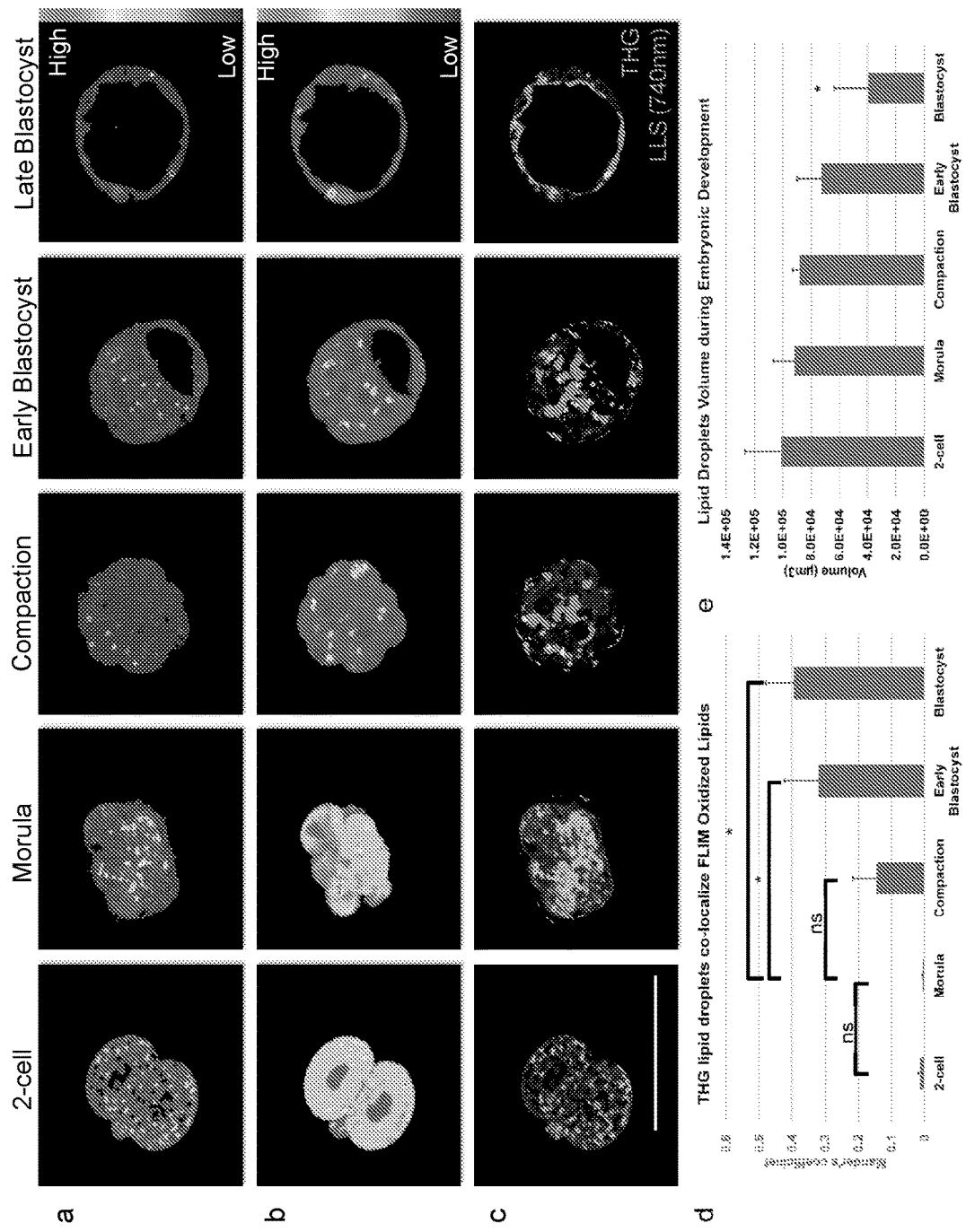
FIG. 9 is a set of images and graphs related to experimental data.

In order to better characterize the lipid droplets distribution during embryonic development, third-harmonic generation (THG) microscopy imaging was employed (see FIG. 9) with a Deep Imaging Via Emission Recovery (DIVER) microscope. The DIVER microscope is an upright laser scanning microscope with a wide photocathode area detector, which allows for collection of photons from a wide area and angle for high efficiency. The third harmonic generation images and intrinsic fluorescence FLIM images were collected using a 40× water immersion objective (Olympus Plan Apo) with 1040 nm and 740 nm excitation respectively. And UG11 and Blue5543 filters were used for THG and endogenous fluorescence FLIM images collection. An a320 FastFLIM FLIMbox (ISS, Champaign, IL) was used to transfer the data to the phasor plot. Rho110 was used for calibration with known lifetime τ=4 ns.

The interfaces heterogeneity can be detected with the third order nonlinearity $\lambda_3$. Given that the process is ultrafast for structures with THG signals, the lifetime is approximately zero. Row A of images shows the representative THG intensity images acquired in the same field of view as that of the FLIM images of row B. The phasor plot of the THG images appears at the coordinate of s=0 and g=1. Furthermore, the co-localization correlation of the long lifetime specie in the FLIM images (red) was correlated with the lipid droplets (green) in THG images (see rows C and D).

During embryonic development, the oxidized lipid signature, color-coded in red for the long lifetime species, (same direction as red arrow 612) accumulated. The Mander's split co-localization correlation coefficients increase from 0.0099 to 0.3907 (where a coefficient of 1 is perfect correlation and 0 is complete lack of correlation) with embryonic development, suggesting that the phasor-FLIM distribution changes during these stages are due to increased lipid accumulation. The lipid droplets distribution during embryonic development was also characterized using the 3D THG image (see row A and graph E in FIG. 9). Cleavage stage embryos have a large amount of small, densely packed lipid droplets, whereas post-cleavage stage embryos have large lipid droplets of the low density. The dramatic changes for both the lipid oxidation and lipid volume size start after compaction stages. These findings demonstrate that the dynamic difference in lipid oxidation can be detected by phasor-FLIM.

Converting FLIM Data onto Phasor Coordinates:

All FLIM images are transformed onto the phasor plot using the equations below. The g and s coordinates are generated from the fluorescence intensity decay of each pixel in the FLIM image using the following Fourier transformation equations (see 201 in FIG. 2):

$$g_i(\omega) = \frac{\int_0^\infty I(t)\cos(\omega t)dt}{\int_0^\infty I(t)dt}$$

$$s_i(\omega) = \frac{\int_0^\infty I(t)\sin(\omega t)dt}{\int_0^\infty I(t)dt}$$

Thus, the phasor approach is a fit-free analysis of FLIM imaging, and the g and s coordinates represent the decay curve at each pixel of the image. Therefore, a phasor analysis transforms the complicated spectrum and decay of each pixel into a unique position on the phasor plot.

Metabolic States in Embryos

Figure 10A:
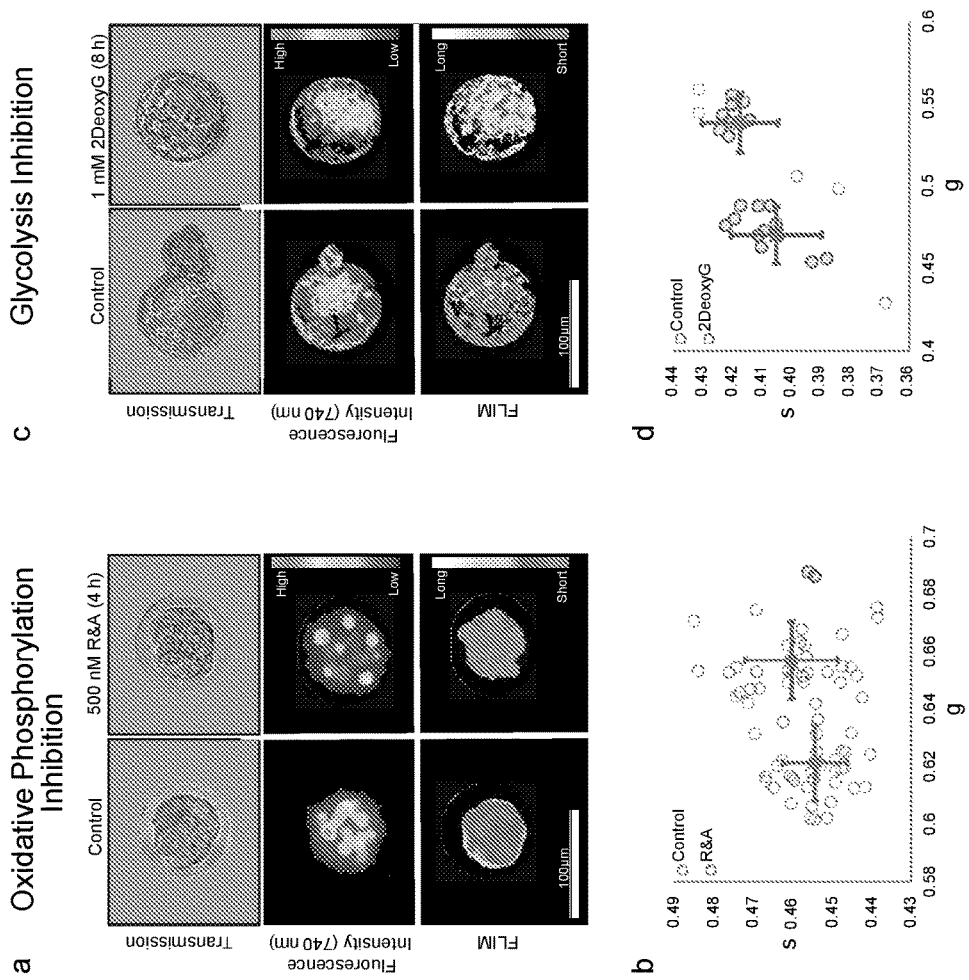
FIG. 10A is a set of images and graphs related to experimental data.

With reference now to FIG. 10A, data is shown indicating that lifetime trajectories reveal metabolic states of pre-implantation mouse embryos. Set of images A comprises transmission (top), fluorescence intensity (middle) and FLIM (bottom) images for control and 4-hour rotenone and antimycin A (R&A) treated embryos. Note a shift from long to short lifetimes (blue to red in FLIM image). Graph B depicts g and s values of control and R&A-treated embryos for individual embryos. Blue circles are controls (n=38), red circles are R&A-treated embryos (n=31), and solid squares and the error bars in the figures means the average and variation of each group (student t-test for g value: p-value=2.86E-16). FLIM images indicate a rightward shift from long to short lifetimes. Set of images C comprises transmission (top), fluorescence intensity (middle) and FLIM (bottom) images for control and 2DeoxyG-treated embryos. Note a shift from long to short lifetimes (red to white in FLIM image). Graph D depicts g and s values of control and 2DeoxyG-treated embryos. Blue squares are controls (n=12), red circles are 2DeoxyG-treated embryos (n=13), and the average of each group can be found in the solid colored squares (student t-test for g value: p-value=3.88E-09). Fluorescence and FLIM images indicate a leftward shift from long to short lifetimes.

The D-trajectory is complex because it is composed of lifetimes from various endogenous fluorescent biochemical species. It was first hypothesized that the major component responsible for the shifts in the D-trajectory was intracellular NADH changes based on its fundamental role in energy production during embryogenesis. To test this hypothesis, the metabolic activity of intracellular NADH was measured. The bound form of NADH is linked to energy production through oxidative phosphorylation, whereas the free form of NADH is associated with glycolysis (see e.g. C. Stringari et al., Metabolic trajectory of cellular differentiation in small intestine by Phasor Fluorescence Lifetime Microscopy of NADH. Sci Rep 2, 568 (2012), incorporated herein by reference). The phasor coordinates of free NADH maps on the right side of the plot with a lifetime of 0.38 ns and the protein bound form of NADH (bound with lactate dehydrogenase) maps on the left at 3.4 ns (see 202 in FIG. 2). This lifetime distribution of the free and bound forms of NADH in the phasor plot have previously been described as the metabolic or M-trajectory.

Next, embryos were treated with known biochemical inhibitors of oxidative phosphorylation and glycolysis. Oxidative phosphorylation was inhibited at the early compaction stage with a cocktail of rotenone and antimycin A (R&A) (500 nM) by inhibiting complex I and complex III of the electron transport chain. Embryos were imaged after a 4-hour culture period (images A in FIG. 10A). The FLIM images show increased fractional contributions of free NADH (shorter lifetimes) when compared to controls (left side images A in FIG. 10A). This shift towards glycolytic metabolism is seen in a dose-dependent manner (see FIG. 10D), indicating that embryos cultured in R&A have decreased oxidative phosphorylation activities (image A and graph B in FIG. 10A). The early blastocyst stage embryos were also cultured in 1 mM 2-Deoxy-D-Glucose (2DeoxyG), an analog of glucose, to inhibit glycolysis (images C of FIG. 10A). The glucose analog treatment shifted the phasor-FLIM distribution to longer lifetime (an increase of bound NADH), which correlates with a decrease in glycolysis (images C and graph D of FIG. 10A). These findings suggest that the source of the changes seen in the phasor coordinates throughout the pre-implantation stages in the D-trajectory is in part due to the contribution from metabolic shifts of NADH.

Figure 10B:
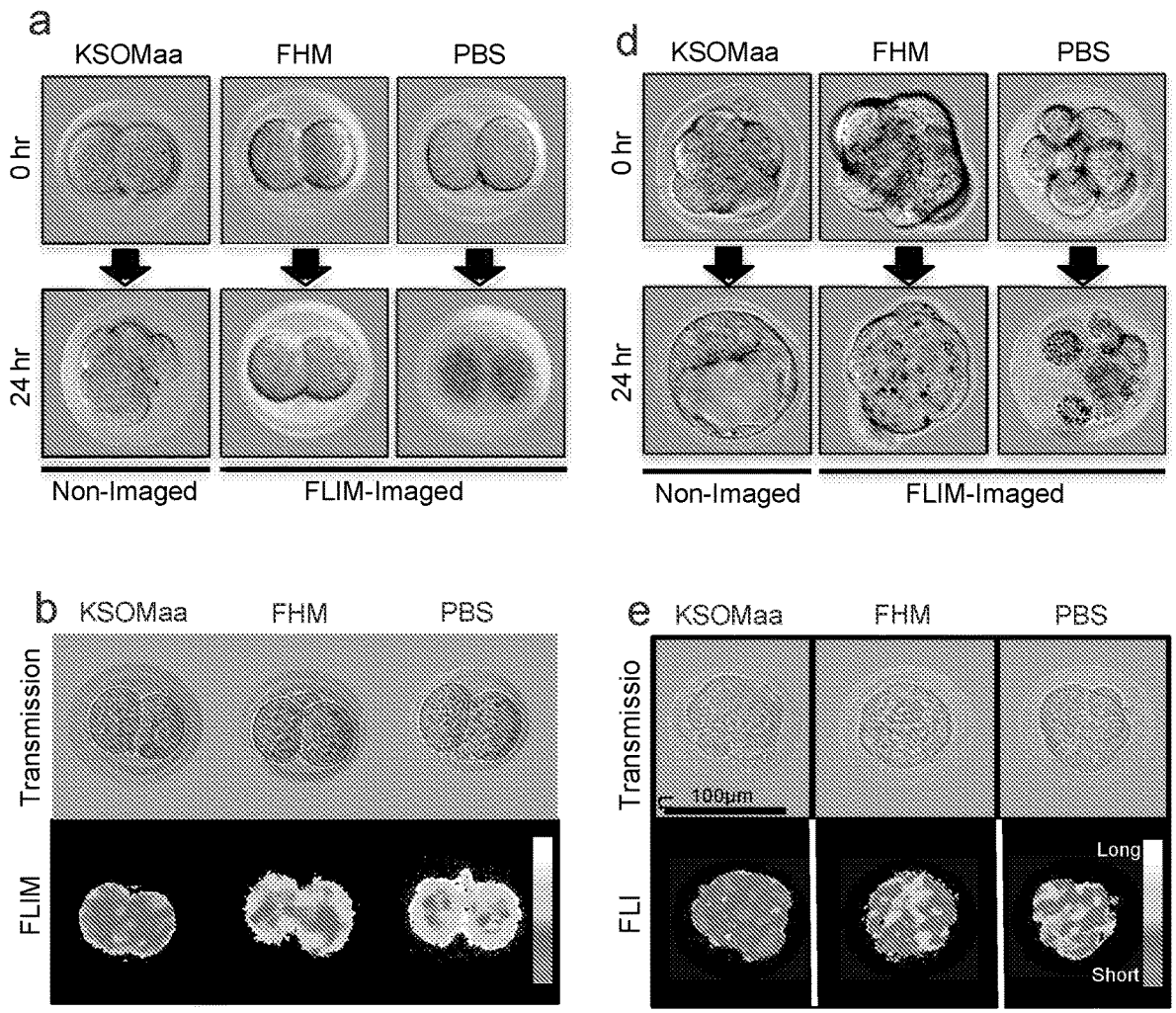
FIG. 10B is a set of images and graphs related to experimental data.
Figure 10C:
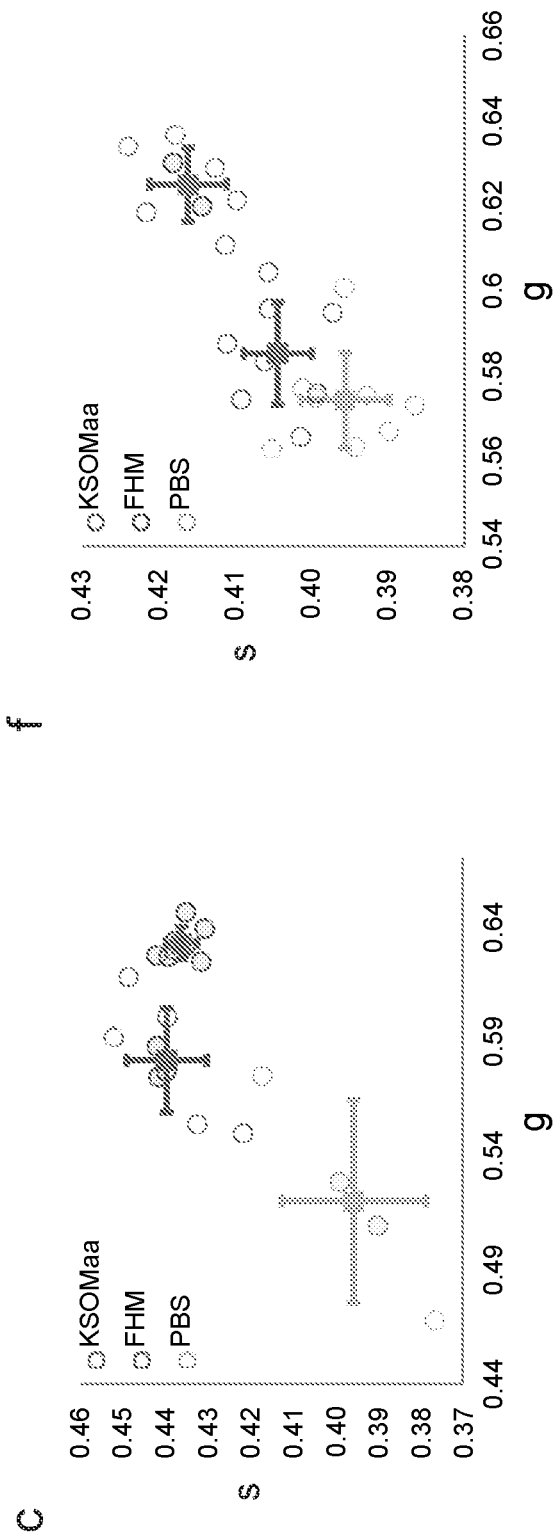
FIG. 10C is a set of graphs related to experimental data.
Figure 10D:
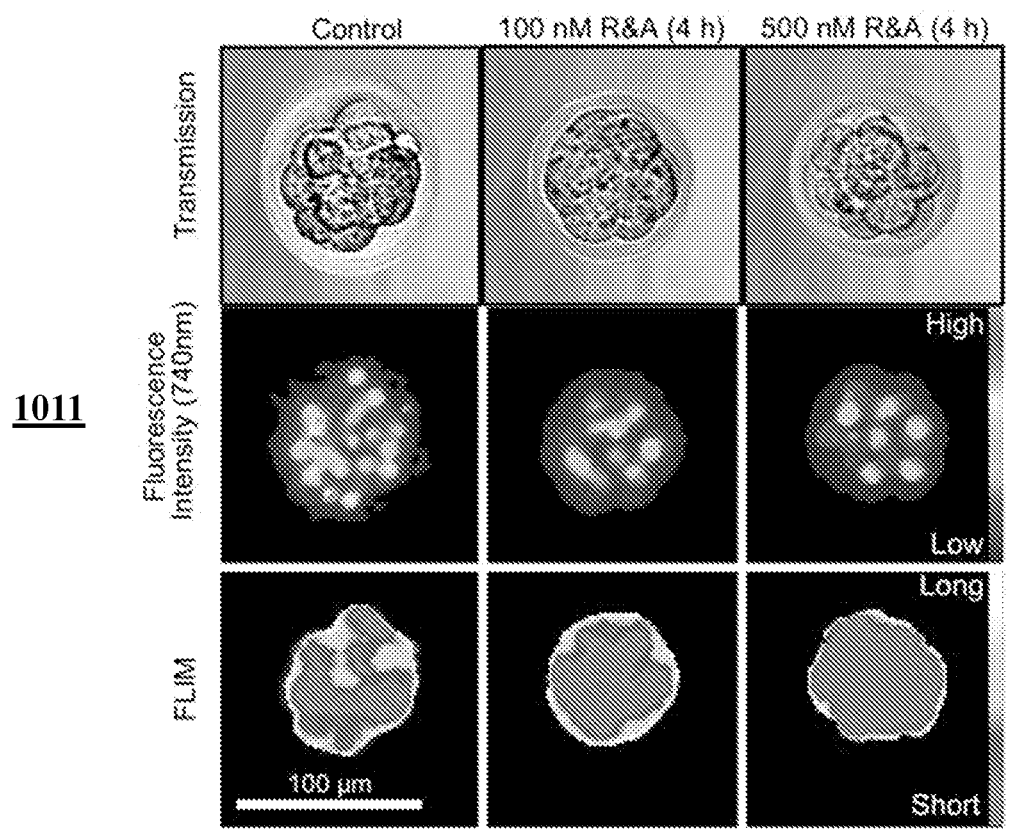
FIG. 10D is a set of images and graphs related to experimental data.
Figure 10D:
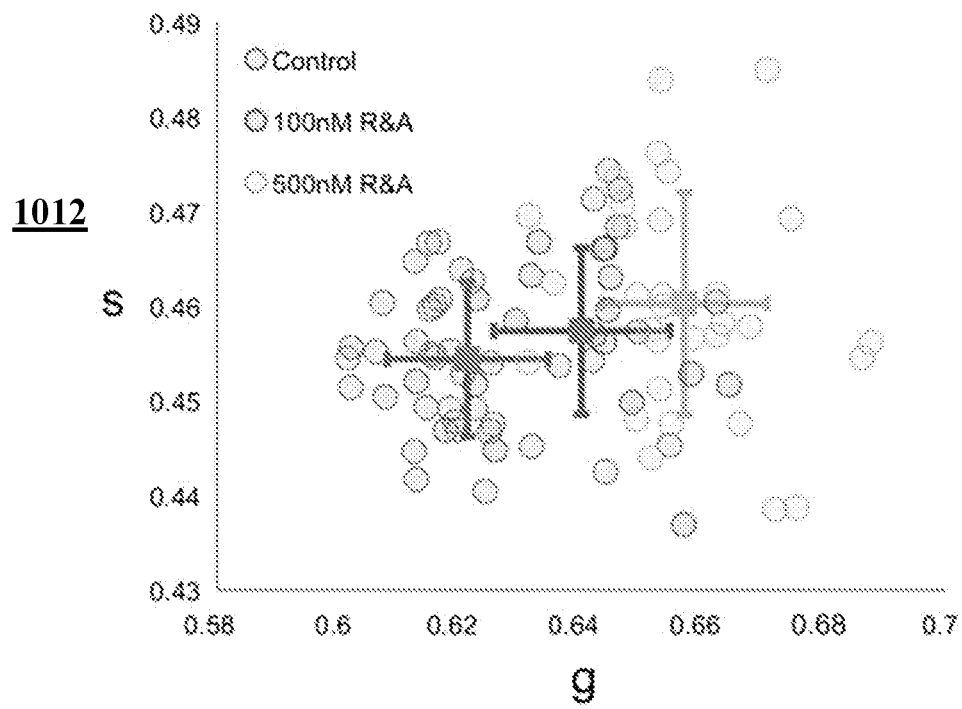

With reference to FIG. 10D, the depicted images and graph demonstrate that fluorescence lifetime trajectories reveal dose-dependent metabolic state changes of pre-implantation mouse embryos. Images 1011 show transmission (top), fluorescence (middle) and FLIM (bottom) images for control and 4-hour 100 nM and 500 nM rotenone and antimycin A (R & A) treated embryos, indicating a shift from long to short lifetimes. Graph 1012 shows g and s values of control and 4-hour 100 nM and 500 nM R&A-treated embryos for individual embryos. Blue circles are controls (n=38), red circles are 4-hour 100 nM R&A-treated embryos (n=21), and green circles are 4-hour 500 nM R&A-treated embryos (n=31). The average of each group can be found in the solid squares (for g value of 100 nM treatment group and 500 nM group compared with control group, p-value=1.76E-5, and 2.86E-16, respectively). FLIM images indicate a rightward shift from long to short lifetimes. Student t-test and two-tail tests were performed.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Identifying Pre-Implantation Embryos Under Stress Conditions

Given that early cleave stage embryos utilize aspartate, pyruvate, and lactate for energy metabolism the next experiment sought to determine whether the unique lifetime distribution patterns of an embryo cultured under altered physiological states can be detected by the changes in spectroscopic distributions of phasor-FLIM.

With reference to FIG. 10B and FIG. 10C, images A show transmission images of embryos collected at the 2-cell stage and cultured in KSOMaa, FHM, or PBS for 24 hours. Images B are representative transmission and FLIM images of embryos in KSOMaa, FHM, or PBS for 4 hours. Graph C in FIG. 10C is a scatter plot of g and s lifetimes collected from a group of embryos cultured in KSOMaa (n=10), FHM (n=10) and PBS (n=4) for 4 hours. p-value=0.0002** and 0.01* (student t-test of g value) for the FHM and PBS group compare with KSOMaa group. Images D are transmission images of embryos collected at the morula stage and cultured in KSOMaa, FHM, or PBS for 24 hours. Images E (FIG. 10B) are representative transmission and FLIM images of embryos in KSOMaa, FHM, or PBS for 4 hours. Graph F in FIG. 10C is a scatter plot of g and s of lifetimes collected from a group of embryos cultured in KSOMaa (n=8), FHM (n=8), and PBS (n=8). p-value=9.29E-06 and 3.21E-07 (student t-test of g value) for the FHM and PBS group compare with KSOMaa group.

2-cell and morula stage embryos were cultured in standard mouse embryo culture media (KSOMaa), flushing and holding media (FHM: DMEM-pyruvate free with HEPES), and saline solution (PBS). Brightfield images and FLIM data were collected at 4 hours and 24 hours after the treatment (FIG. 10B). The FLIM data were collected once at the first time-point (4 hours). The 2-cell stage embryos cultured under KSOMaa, FHM and PBS were morphologically normal (Images A, top row of FIG. 10B). However, the embryos in high-stress conditions (FHM and PBS) show distinct lifetime distribution patterns on the phasor-plot when compared to that of KSOMaa cultured embryos (Images B of FIG. 10B and graph C of FIG. 10C, Graph A of FIG. 10E). Subsequently, the embryos under high-stress conditions were found to fail to cleave normally and remain at the 2-cell stage, unlike KSOMaa controls (images B in FIG. 10B, Graph A of FIG. 10E). Similar analysis using compaction stage embryos was performed, and it was observed that within a few hours under high-stress culture conditions, the phasor-FLIM lifetime trajectories of embryos deviate from those cultured in KSOMaa even before the embryos show any signs of abnormal morphology (Images D and E of FIG. 10B, graph F of FIG. 10C, Graph B of FIG. 10E). The cell division in FHM and PBS cultured embryos also slowed down significantly (Graph B of FIG. 10E).

Figure 10E:
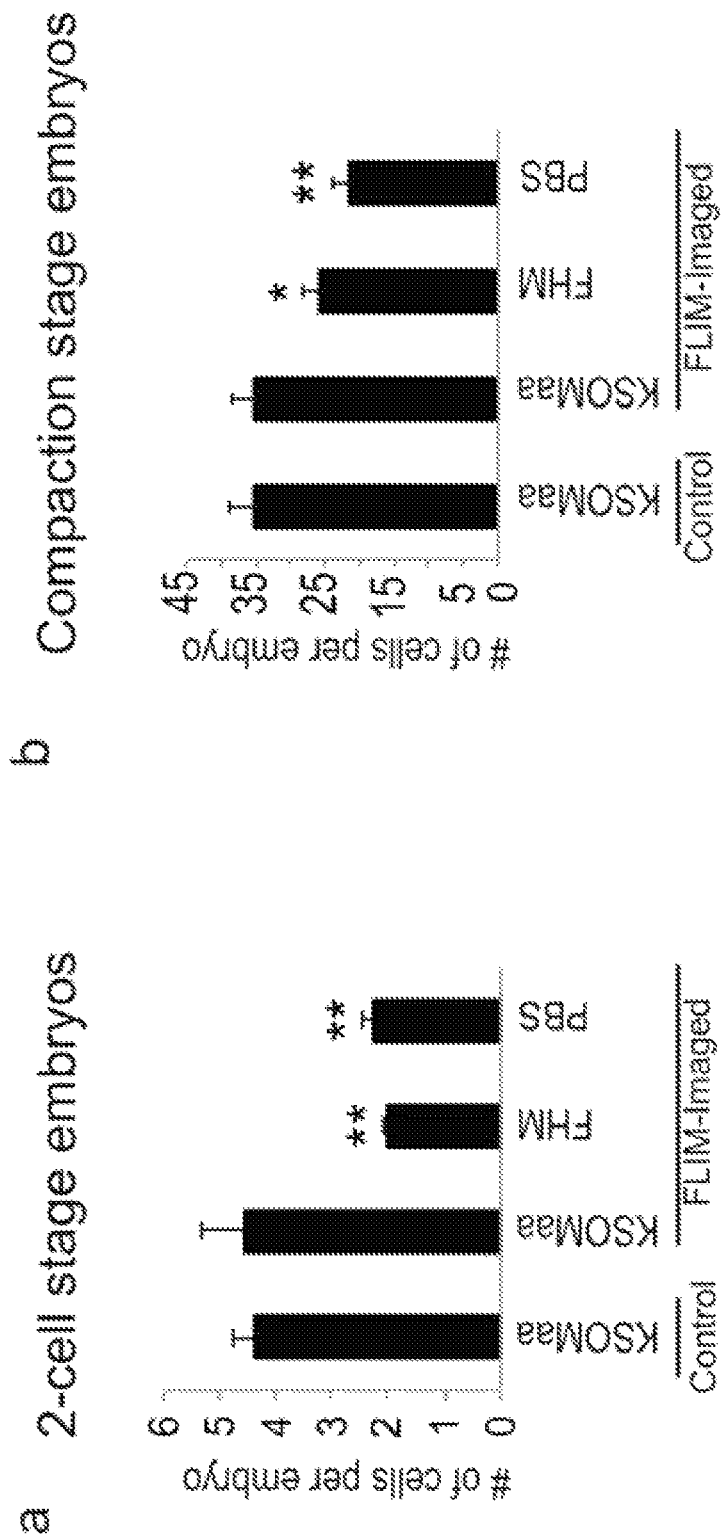
FIG. 10E is a set of graphs related to experimental data.

With reference to FIG. 10E, two graphs A and B are shown depicting the average number of cells per embryo cultured under high stress conditions. Bar graph A shows the average number of cells present in an embryo after xx hours of culturing in the indicated media starting at the 2-cell stage. KSOMaa non-image control (n=8), KSOMaa (n=10), FHM (n=11), PBS (n=11), compare to the results from KSOMaa group, p-value=0.004 and 0.001 for FHM and PBS, respectively. Bar graph B shows the average number of cells per embryo after continuous culturing of embryos in the indicated media starting at the morula stage. KSOMaa non-image control (n=10), KSOMaa (n=18), FHM (n=11), PBS (n=11), p-value=0.002** and 0.02* for FHM and PBS, respectively.

It was concluded that phasor-FLIM is a sensitive method to detect the changes in embryo metabolism upon cellular stress.

Derivation of the Embryo Vitality Index

Figure 11A:
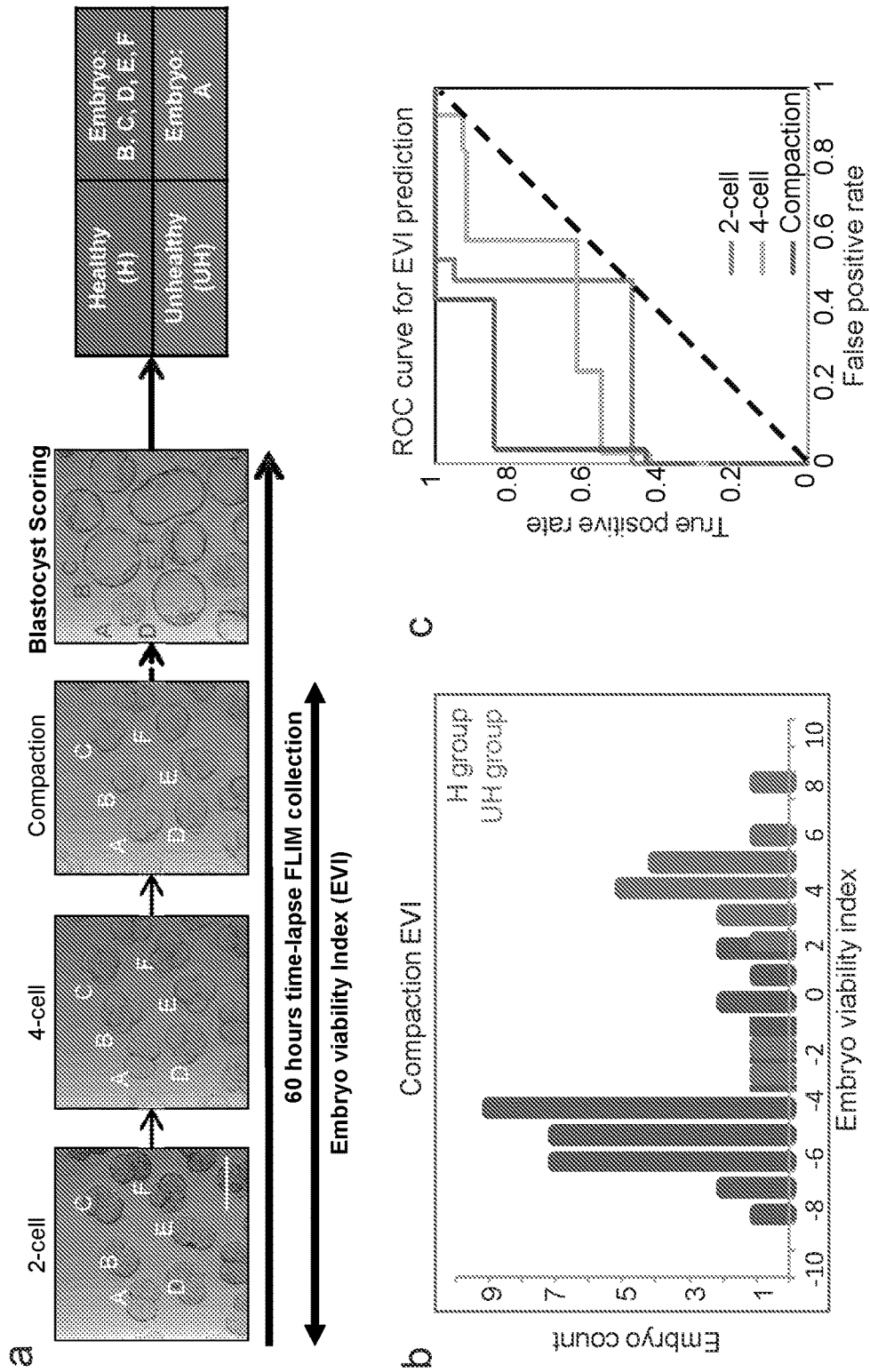
FIG. 11A is a set of images and graphs related to experimental data.
Figure 11B:
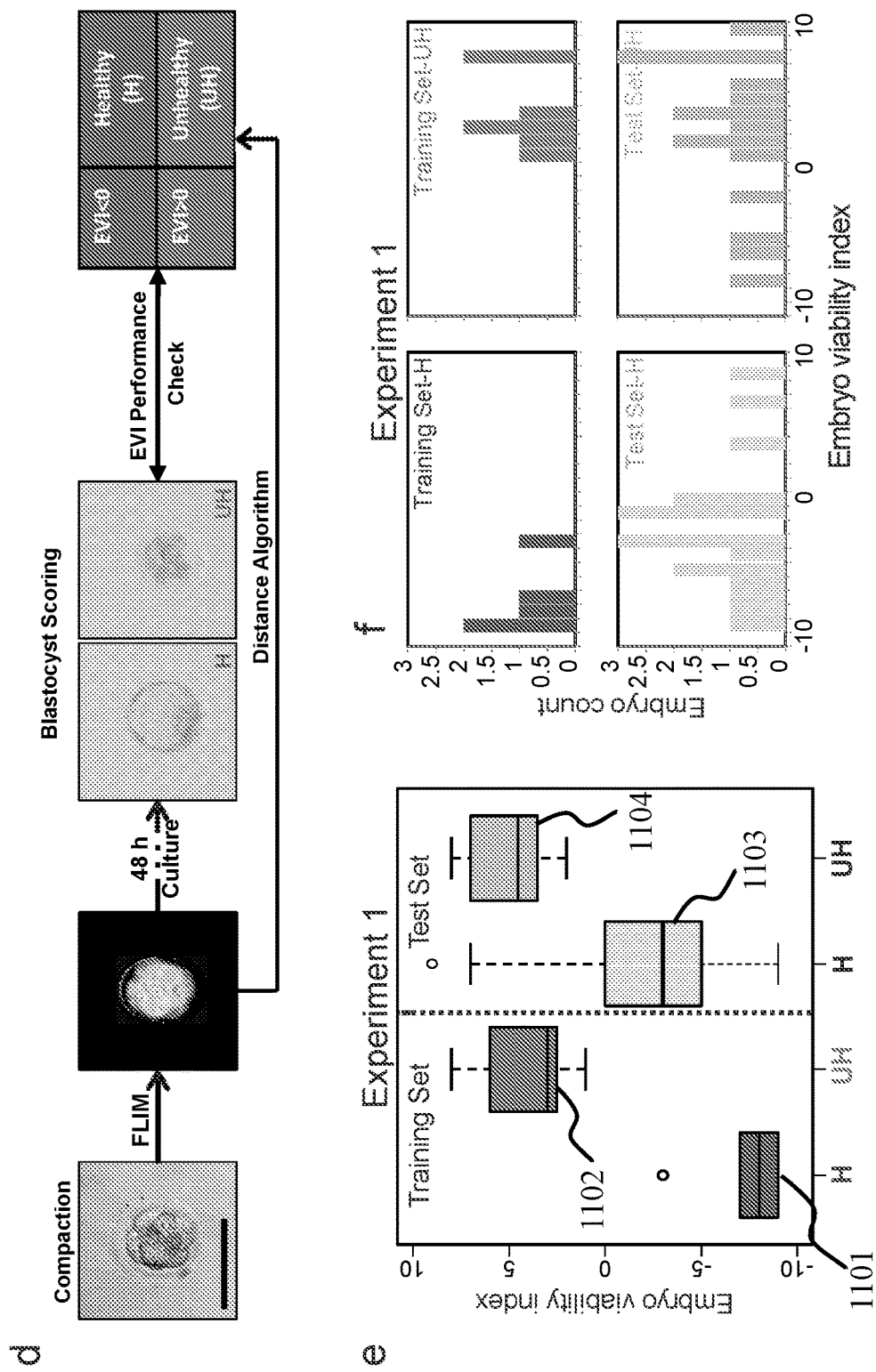
FIG. 11B is a set of images and graphs related to experimental data.

The phasor distribution analysis of pre-implantation mouse embryos allows differentiation between normal and highly stressed embryos (see FIG. 11A and FIG. 11B).

With reference now to FIG. 11A, element A shows a schematic of the experimental setup used to generate the subsequent data. Individual embryos (A-F) were followed from the 2-cell to blastocyst stage and classified as healthy (H) and unhealthy (UH) group according to their morphology at E4.5. Histogram B is a graph of embryo viability index (EVI) of early compaction embryos from one representative experiment (H group, n=37; UH group, n=27). The blue and red bars represent the embryo condition determined as healthy and unhealthy at ~60 hours after FLIM imaging at the pre-compaction stage. Graph C is a receiver operating characteristic (ROC) curve, showing the performance of the binary classification model developed from lifetime distribution patterns of early developmental stage embryos (2-cell, 4-cell, and early compaction stage). The area under the curve for each stage is 0.739 (2-cell), 0.728 (4-cell) and 0.916 (early compaction). The dashed line in the diagonal is presented as a random bi-classification model. With reference to FIG. 11B, Element D is a schematic of a FLIM-Distance Analysis Pipeline. Box-whisker plots E show a training set of healthy (n=5) and unhealthy (n=7) groups and tested unknowns of healthy (n=18) and unhealthy (n=16) embryos. Bar graph F shows the embryo viability index of the embryos shown in element E. The training set H is in navy, training set UH is in red. Testing set H is in light blue, and Testing set U is in orange.

The results show that the developmental potential of pre-implantation embryos is predictable through phasor-FLIM analysis. Time-lapse phasor-FLIM imaging of embryos was performed from the 2-cell stage for ~60 hours to identify the most desirable stage to predict the developmental potential of embryos (element A). At the end of the 60-hour culture period, embryos were classified as healthy (H) if they reached the normal full expanded blastocyst stage showing a tightly packed ICM and cohesive epithelium shaped TE cells, or not healthy (UH) if embryos were arrested before reaching the blastocyst stage or displaying abnormal blastocyst morphology (element A). The distance analysis (DA) algorithm was then applied to identify key spectroscopic parameters that could differentiate healthy (H) from unhealthy (UH) embryos by machine learning (see Ranjit et al., Characterizing fibrosis in UUO mice model using multiparametric analysis of phasor distribution from FLIM images. Biomedical Optics Express 7, 3519-3530 (2016), incorporated herein by reference).

Using the DA algorithm, the 3D phasor histogram was separated into 4 sections based on the phasor coordinates (g, s) intensity, from which, 6 parameters were extracted from each section, generating a total of 24 parameters. The healthy embryos (H group) were used as the control set and the unhealthy embryos (UH group) were used as the sample set. Each of these sets included images from multiple embryos from each stage in development. Next, the average and variance of the training set were calculated, which includes two groups (H and UH), and weighted 20 parameters (g, s, the secondary moment a, b and angle from 4 sub-layers, intensity excluded) in each set from the 3D phasor plot. After optimizing the weights to maximize the difference between unhealthy and healthy group embryos, the weights were applied to index a new score called the EVI or Embryo Viability Index. This partition metric defines the degree of separation of the test embryos from the average of the training set where −1 to −10 are unhealthy embryos, and +1 to +10 are healthy embryos.

Figure 11C:
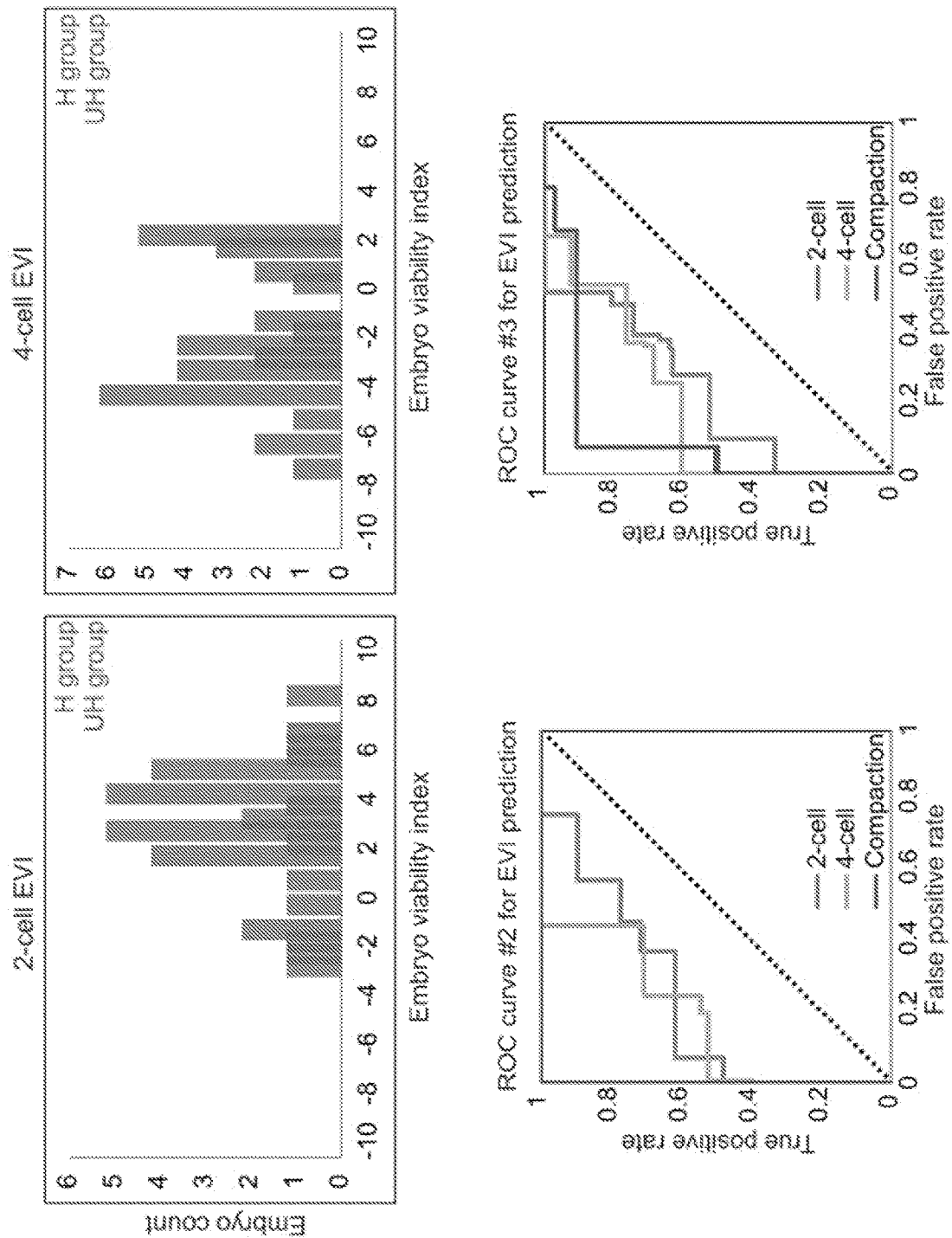
FIG. 11C is a set of graphs related to experimental data.

Next, the DA data from 2-cell, 4-cell, and the early compaction stage was examined to determine the best binary classification model using receiver operating characteristic (ROC) curves (Graphs B and C in FIG. 11A, Graphs A and B in FIG. 11C). The embryos predicted to be healthy were classified in positive values (EVI<0, in blue), and embryos predicted to be unhealthy in negative values (EVI>0, in red). The plot of true positive rates against false positive rates gives an area under the ROC curve (AUC) for 2-cell, 4-cell, and the early compaction stage embryos, which were 0.739, 0.728, and 0.916, respectively. It was therefore concluded that the spectroscopic characteristics of the early compaction stage embryos (prediction accuracy with the highest AUC) possess the best parameters for separating embryos that will develop into normal blastocysts (Graphs B and C in FIG. 11A, Graphs A and B in FIG. 11C).

With reference to FIG. 11C, the presented data shows that the embryo viability index of morula shows the potential to distinguish healthy and unhealthy pre-cleavage stage embryos. Graphs A are histograms of embryo viability index of 2-cell and morula stage embryos from one representative experiment (2-cell EVI: H group, (n=18), UH group, (n=17). 4-cell EVI, H group, (n=25), UH group, (n=9)). Each blue and red bar represents the morula stage FLIM-fingerprints of healthy (H) and unhealthy (UH) embryos at 60 hours after imaging respectively. Graphs B are receiver operating characteristic (ROC) curves showing the performance of the binary classification model developed from lifetime distribution patterns of pre-compaction stage embryos (2-, 4-, and early compaction) of two time-lapse FLIM tracking experiments. The area under curve for each stage is 0.777 (2-cell, H n=37; UH, n=8), 0.823 (4-cell, H, n=45; UH, n=8) and 1.000 (early compaction, H, n=30; UH, n=2) for experiment 2, and 0.777 (2-cell, H, n=38, UH, n=10), 0.813 (4-cell, H, n=39, UH, n=7) and 0.945 (early compaction, H, n=39, UH, n=6) for experiment 3.

An embryo viability prediction pipeline was developed based on the DA of phasor-FLIM images of the early compaction stage embryos (Diagram D, FIG. 11B). FLIM images of embryos at the early compaction stage were recorded and all said embryos were allowed to develop to the blastocyst equivalent stage. The resulting embryos were classified as H or UH. A small number of healthy (H) and unhealthy (UH) embryos were then selected as an EVI training data set. The remaining unselected embryos were also subjected to the DA program as "unknowns" (test set) to test the predictability of EVI. The development of 35 morphologically healthy looking early compaction stage embryos (pooled from 4 mating pairs) was followed and recorded, until the blastocyst stage (Graphs E and F, FIG. 11B). Of the 34 embryos, 18 developed to normal blastocysts and thus assigned as healthy (H), and 16 embryos that failed to reach the blastocyst were assigned as unhealthy (UH). When EVIs that were determined by the training set were applied, 83.3% of healthy embryos (15 out of 18 embryos) and 75.0% of unhealthy embryos (12 out of 16 embryos) were correctly identified by EVI (Graphs E and F). Subsequently, four biologically independent experiments were performed using a total of 134 embryos, with the results shown in Table 4 below and FIG. 11D. The results show 85.9% accuracy (n=134) where a total of 88.5% healthy embryos (n=96) and 73.7% unhealthy embryos (n=38) were identified. Based on the results, it was concluded that the DA program is able to predict the development potential of pre-implantation embryos at the early compaction stage.\

Figure 11D:
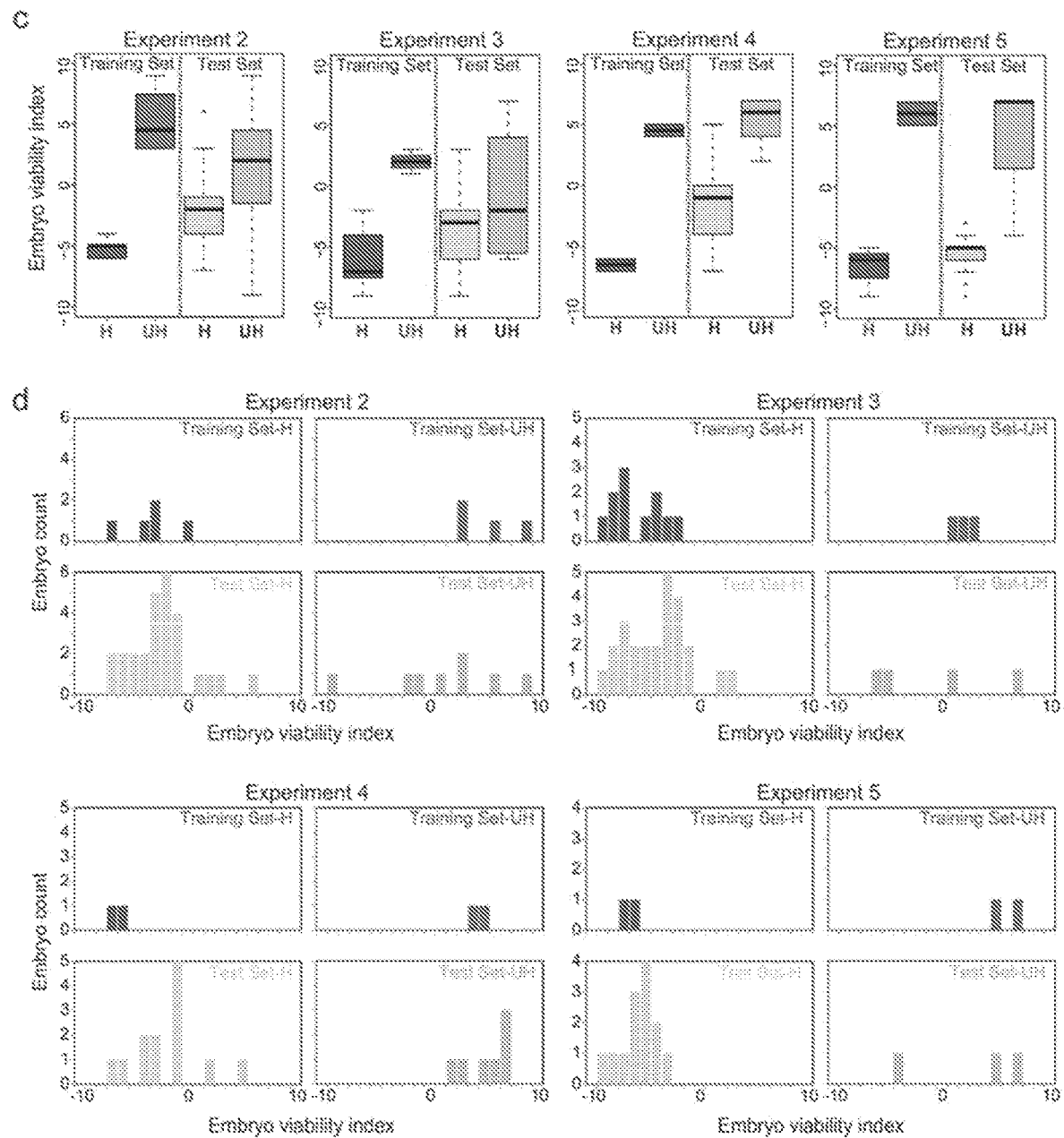
FIG. 11D is a set of graphs related to experimental data.

With reference to FIG. 11D, Box-whisker plots C show training sets of healthy (H) and unhealthy (UH) groups and predication performance on tested embryos for 4 additional experiments. The training set H is in navy, Training set UH in red, predicated healthy in light blue, and predicated unhealthy in orange. The n number for the training set healthy group was n=11, 2 and 3. The n number for the training set unhealthy group was n=4, 3, 2, and 2. The n number for the test unknown healthy group was n=27, 25, 13, and 13. The n number for the test unknown unhealthy group was n=8, 4, 7, and 3. Bar graphs D show the embryo viability index of experiments 2, 3, 4 and 5. The training set H is in navy, Training set UHs in red, Healthy in light blue, and Unhealthy in orange.

TABLE 4

|  | False Positive Rate | True Positive Rate | Accuracy | Precision | Sensitivity | Specificity |
| --- | --- | --- | --- | --- | --- | --- |
| Experiment 1 | 0.250 | 0.833 | 0.794 | 0.789 | 0.833 | 0.750 |
| Experiment 2 | 0.375 | 0.852 | 0.800 | 0.885 | 0.852 | 0.625 |
| Experiment 3 | 0.500 | 0.920 | 0.862 | 0.920 | 0.920 | 0.500 |
| Experiment 4 | 0.000 | 0.846 | 0.900 | 1.000 | 0.846 | 1.000 |
| Experiment 5 | 0.333 | 1.000 | 0.938 | 0.929 | 1.000 | 0.667 |
|  | 0.292 | 0.890 | 0.859 | 0.905 | 0.890 | 0.708 |

Statistical Analysis

Data are presented as mean±standard deviation. For the FLIM data, the statistical analyses were performed using student t-test for the g value only, $p<0.05$ was considered as statistically significant.

The box-whisker plot showing the prediction ability represents the median ±min/max from each indicated group (Training set H and UH group, Tested H and UH group).

DISCUSSION

The disclosed experiments show that phasor-FLIM represents a promising new approach for assessing the quality of pre-implantation mouse embryos. The phasor-FLIM analysis was applied to capture developmental states during pre-implantation development. The spectroscopic trajectory, referred to herein as the "D-trajectory" (D for development), is attributed to a combination of metabolic fluorescent species and production of ROS in conjunction with oxidized lipid metabolism within the embryo (see graphs C and D, FIG. 6B), and this trajectory correlates well with other measurements of embryonic development. Second, the intrinsic lifetime trajectory of pre-implantation embryos cultured in nutrient-deficient media deviates from the normal lifetime distribution, indicating that the lifetime trajectory can be used to detect metabolic changes in embryos. Third, the applied DA program uses spectroscopic parameters from 3D phasor histograms of embryos, and shows that EVI is a non-morphological, quantitative index that can provide useful information on the quality of pre-implantation embryos.

Results

By implementing the phasor-FLIM information into a Distance Machine Learning Program, 86% (n=133) prediction accuracy was achieved for mouse embryo developmental potential prediction. The results are shown in FIG. 11B. The data for the training set is shown in box and whisker plot 1101 for healthy embryos and plot 1102 for unhealthy embryos. The data for the test set is shown in box and whisker plot 1103 for healthy embryos and plot 1104 for unhealthy embryos. 93% of the training set and 89% of the test set were correctly predicted. Data was measured at the compaction stage, which is 48 hours ahead of the traditional observation time point. Thus, FLIM analysis provides a potential new format for selecting healthy embryos for implantation and represents an improvement over the state of the art in ART. The disclosed imaging device is advantageous over existing devices due to the collection of non-invasive, quantitative and real-time metabolic information.

acquiring a set of images of the tissue from an imaging device;
performing a Fourier Transformation on the set of images to generate a set of phasor coordinates;
computing a D-trajectory of the phasor coordinates;
computing a set of values of additional parameters selected from the group consisting of coordinates for a center of mass g and s, second axial moments a and b after diagonalization, an angle of distribution from diagonalization, and a total number of pixels in the phasor plot from slices derived from the phasor coordinates from the set of images and the phasor coordinates;
comparing the set of values to a set of stored values related to tissues having one or more known characteristics; and
calculating one or more properties of the tissue from the set of values and the set of stored values.

2. The method of claim 1, wherein the values of additional parameters comprise changes in metabolism of at least one cell in the tissue, and the properties of the tissue are selected from the group consisting of cell cycle, stress, cancer, and diabetes.

3. The method of claim 1, wherein the tissue is taken from a blood sample, and the properties of the tissue are indicative of a neurodegenerative disease.

4. The method of claim 1, wherein the excitation energy is selected from the group consisting of laser light, LED

What is claimed is:

1. A method for determining one or more properties of a tissue, comprising:
    exciting a tissue with an excitation energy from an excitation source at an excitation frequency;

light, photon laser light, photon excitation laser light, and diffuse light.

5. The method of claim 1, wherein the excitation energy source is selected from the group consisting of a laser source, an LED source, and a lamp.

6. The method of claim 1, further comprising a step of preventing excessive heating of the embryo by the excitation source with an excitation cleaner.

7. The method of claim 6, wherein the excitation cleaner is selected from the group consisting of a heat blocker, a bandpass filter, a low-pass filter, a high-pass filter, a filter wheel, and beam splitter glass.

8. The method of claim 1, wherein the imaging device is selected from the group consisting of a modulated CMOS camera, a modulated EMCCD, an intensified CCD, a PMT, an APD, and a SPAD.

9. The method of claim 1, wherein the imaging device comprises a microscope.

10. The method of claim 1, wherein the imaging device is selected from the group consisting of a scanning device, a camera, a FLIM acquisition peripheral, and a point detector.

11. The method of claim 1, wherein the imaging device is a fluorescence lifetime imaging microscope.

12. The method of claim 1, further comprising the step of modulating the excitation source at a frequency in a range from 1 MHz to 1 GHz.

13. The method of claim 1, further comprising the step of acquiring multiple images from the imaging device simultaneously, wherein the imaging device is a CMOS imaging device having a plurality of taps.

14. The method of claim 13, wherein the imaging device is selected from a modulated CMOS camera, a modulated EMCCD, an intensified CCD, a PMT, an APD, or a SPAD.

* * * * *